United States Patent
Herr et al.

(10) Patent No.: US 10,993,639 B2
(45) Date of Patent: May 4, 2021

(54) FEEDBACK METHOD AND WEARABLE DEVICE TO MONITOR AND MODULATE KNEE ADDUCTION MOMENT

(71) Applicant: Massachusetts Institute Of Technology, Cambridge, MA (US)

(72) Inventors: Hugh Miller Herr, Somerville, MA (US); Madeleine Rose Abromowitz, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 222 days.

(21) Appl. No.: 15/306,299

(22) PCT Filed: Apr. 24, 2015

(86) PCT No.: PCT/US2015/027460
§ 371 (c)(1),
(2) Date: Oct. 24, 2016

(87) PCT Pub. No.: WO2015/164706
PCT Pub. Date: Oct. 29, 2015

(65) Prior Publication Data
US 2017/0042467 A1    Feb. 16, 2017

Related U.S. Application Data

(60) Provisional application No. 61/984,204, filed on Apr. 25, 2014.

(51) Int. Cl.
*A61B 5/11*    (2006.01)
*A61B 5/00*    (2006.01)
(Continued)

(52) U.S. Cl.
CPC ............ *A61B 5/112* (2013.01); *A61B 5/1121* (2013.01); *A61B 5/4585* (2013.01); *A61B 5/486* (2013.01);
(Continued)

(58) Field of Classification Search
CPC .................. A61B 5/486; A61B 5/1121; A61B 5/1123–1128; A61B 5/725; A61B 5/4585; A61B 5/112; A61B 2562/0219
See application file for complete search history.

(56) References Cited

U.S. PATENT DOCUMENTS

| 7,291,119 B1 | 11/2007 | De Guise et al. |
| 7,481,780 B2 | 1/2009 | De Guise et al. |

(Continued)

FOREIGN PATENT DOCUMENTS

WO    WO 2015/164706 A1    10/2015

OTHER PUBLICATIONS

Shull, Pete, et al. "Haptic Gait Retraining for Knee Osteoarthritis Treatment." 2010 IEEE Haptics Symposium, 2010, doi:10.1109/haptic.2010.5444625. (Year: 2010).*

(Continued)

*Primary Examiner* — Daniel L Cerioni
*Assistant Examiner* — Raymond P Dulman
(74) *Attorney, Agent, or Firm* — Hamilton, Brook, Smith & Reynolds, P.C.

(57) ABSTRACT

Knee adduction moment of an untethered human during gait is modulated by determining at least one feature associated with instantaneous knee adduction moment of the untethered human during a gait cycle. Feedback to be transmitted to the human is, optionally, derived from the feature, such as by comparing the at least one feature to a value, such as a target value. The feature, or feedback derived from the feature, is transmitted to the human for response by the human, thereby (Continued)

modulating knee adduction moment of the untethered human during the gait.

29 Claims, 11 Drawing Sheets

(51) Int. Cl.
  A61F 2/60 (2006.01)
  A61F 2/70 (2006.01)
(52) U.S. Cl.
  CPC .......... *A61B 5/6828* (2013.01); *A61B 5/6829* (2013.01); *A61B 5/725* (2013.01); *A61B 5/7271* (2013.01); *A61B 5/742* (2013.01); *A61B 5/7405* (2013.01); *A61B 5/7455* (2013.01); *A61F 2/60* (2013.01); *A61F 2/70* (2013.01); *A61B 2562/0219* (2013.01); *A61B 2562/0223* (2013.01); *A61B 2562/0247* (2013.01)

(56) References Cited

U.S. PATENT DOCUMENTS

| | | | | |
|---|---|---|---|---|
| 2003/0083596 | A1* | 5/2003 | Kramer | A61B 5/6804 600/595 |
| 2007/0084278 | A1* | 4/2007 | Kawal | A61B 5/1038 73/172 |
| 2011/0270132 | A1* | 11/2011 | Mezghani | A61B 5/4585 600/587 |
| 2012/0255160 | A1 | 10/2012 | Boone et al. | |
| 2012/0277063 | A1* | 11/2012 | Zhang | A61B 5/4585 482/8 |
| 2013/0204545 | A1* | 8/2013 | Solinsky | G01P 13/00 702/44 |
| 2013/0217998 | A1* | 8/2013 | Mahfouz | G16H 50/50 600/409 |

OTHER PUBLICATIONS

Herr, H., and M. Popovic. "Angular Momentum in Human Walking." Journal of Experimental Biology, vol. 211, No. 4, 2008, pp. 467-481., doi:10.1242/jeb.008573. (Year: 2008).*
Savelberg, et al., Assessment of the horizontal, fore-aft component of the ground reaction force from insole pressure patterns by using artificial neural networks, 1999, Clinical Biomechanics, 14, p. 585-592 (Year: 1999).*
Bae, J., Kong, K., Byl, N., & Tomizuka, M. (2011). A mobile gait monitoring system for abnormal gait diagnosis and rehabilitation: a pilot study for Parkinson disease patients. *Journal of Biomechanical Engineering*. doi: 10.1115/1.4003525.
Bark, K., Wheeler, J., Lee, G., Savall, J., & Cutkosky, M. (2009). A wearable skin stretch device for haptic feedback. *World Haptics 2009—Third Joint EuroHaptics Conference and Symposium on Haptic Interfaces for Virtual Environment and Teleoperator Systems*. doi:10.11 09/WHC.2009.481 0850.
Collins, A. T., Blackburn, J. T., Olcott, C. W., Miles, J., Jordan, J., Dirschl, D. R., & Weinhold, P. S. (2011 ). Stochastic resonance electrical stimulation to improve proprioception in knee osteoarthritis. *The Knee*, 18, 317-322. doi:10.1016/j.knee.2010.07.001.
Cook, C., Pietrobon, R., & Hegedus, E. (2007). Osteoarthritis and the impact on quality of life health indicators. *Rheumatology International*, 27(4), 315-21. doi: 1 0.1 007/s00296-006-0269-2.
Cordero, A. Forner, Koopman, H. J. F. M., & van der Helm, F. C. T. (2004). Use of pressure insoles to calculate the complete ground reaction forces. *Journal of Biomechanics*, 37(9), 1427-32. doi:10.1 016/j.jbiomech.2003.12.016.
Dowling, A. V, Fisher, D. S., & Andriacchi, T. P. (2010). Gait modification via verbal instruction and an active feedback system to reduce peak knee adduction moment. *Journal of Biomechanical Engineering*, 132(7), 071007. doi: 1 0.1115/1.4001584.
Fong, D. T.-P., Chan, Y.-Y., Hong, Y., Yung, P. S.-H., Fung, K.-Y., & Chan, K.-M. (2008). Estimating the complete ground reaction forces with pressure insoles in walking. *Journal of Biomechanics*, 41, 2597-2601. doi: 10.1 016/j.jbiomech.2008.05.007.
Foroughi, N., Smith, R., & Vanwanseele, B. (2009). The association of external knee adduction moment with biomechanical variables in osteoarthritis: a systematic review. *The Knee*, 16(5), 303-9. doi:1 0.1 016/j.knee.2008.12.007.
Franz, J. R., Maletis, M., & Kram, R. (2014). Real-time feedback enhances forward propulsion during walking in old adults. *Clinical Biomechanics (Bristol, Avon)*, 29(1), 68-74. doi:10.1016/j.clinbiomech. 2013.10.018.
Fregly, B. J., Reinbolt, J. A., Rooney, K. L., Mitchell, K. H., & Chmielewski, T. L. (2007). Design of patient specific gait modifications for knee osteoarthritis rehabilitation. *IEEE Transactions on Bio-Medical Engineering*, 54(9), 1687-1695. doi:10.1109/TBME. 2007.891934.
Guccione, a a, Felson, D. T., & Anderson, J. J. (1990). Defining arthritis and measuring functional status in elders: methodological issues in the study of disease and physical disability. *American Journal of Public Health*, 80(8), 945-9. Retrieved from http://www.pubmedcentral.nih.gov/articlerender.fcgi?artid=1404793&tool=pmcentrez&rendertype=abstract.
Jackson, B. D., Wluka, A. E., Teichtahl, A. J., Morris, M. E., & Cicuttini, F. M. (2004). Reviewing knee osteoarthritis—a biomechanical perspective. Journal of Science and Medicine in Sport / Sports Medicine Australia, 7, 347-357. doi:10.1016/S1440-2440(04)80030-6.
Kalman, R. E. (1960). A New Approach to Linear Filtering and Prediction Problems. Transactions of the ASME-Journal of Basic Engineering, 82, 35-45. doi:10.1115/1.3662552.
Kesar, T. M., Perumal, R., Reisman, D. S. et al (2009). Functional electrical stimulation of ankle plantarflexor and dorsiflexor muscles: effects on poststroke gait. Stroke; a Journal of Cerebral Circulation, 40(12), 3821-3827. doi:10.1161/STROKEAHA.109.560375.
Minetti, A. E., Cisotti, C., & Mian, O. S. (2011). The mathematical description of the body centre of mass 3D path in human and animal locomotion. Journal of Biomechanics, 44, 1471-1477. doi:10.1016/j.jbiomech.2011.03.014.
Morgenroth, D. C., Segal, A. D., Zelik, K. E. et al (2011). The effect of prosthetic foot push-off on mechanical loading associated with knee osteoarthritis in lower extremity amputees. Gait & Posture. doi:10.1016/j.gaitpost.2011.07.001.
Norvell, D. C., Czerniecki, J. M., Reiber, G. E., Maynard, C., Pecoraro, J. A, & Weiss, N. S. (2005). The prevalence of knee pain and symptomatic knee osteoarthritis among veteran traumatic amputees and nonamputees. Archives of Physical Medicine and Rehabilitation, 86(3), 487-93. doi:10.1016/j.apmr.2004.04.034.
Peckham, P. H., & Knutson, J. S. (2005). Functional electrical stimulation for neuromuscular applications. Annual Review of Biomedical Engineering, 7, 327-60. doi:10.1146/annurev.bioeng.6. 040803.140103.
Robbins, S. M. K., Birmingham, T. B., Maly, M. R., Chesworth, B. M., & Giffin, J. R. (2011). Comparative diagnostic accuracy of knee adduction moments in knee osteoarthritis: a case for not normalizing to body size. Journal of Biomechanics, 44, 968-971. doi:10. 1016/j.jbiomech.2010.12.021.
Sharma, L., Hurwitz, D. E., Thonar, E. J. et al (1998). Knee adduction moment, serum hyaluronan level, and disease severity in medial tibiofemoral osteoarthritis. Arthritis and Rheumatism, 41, 1233-1240. doi:10.1002/1529-0131(199807)41:7<1233::AID-ART14>3.0.CO<http://3.0.CO>;2-L.
Shull, P. B., Lurie, K. L., Cutkosky, M. R., & Besier, T. F. (2011). Training multi-parameter gaits to reduce the knee adduction moment with data-driven models and haptic feedback. Journal of Biomechanics, 44(8), 1605-9. doi:10.1016/j.jbiomech.2011.03.016.
Weinstein, A. M., Rome, B. N., Reichmann, W. M. et al (2013). Estimating the burden of total knee replacement in the United States. The Journal of Bone and Joint Surgery. American Volume, 95(5), 385-92. Retrieved from http://www.ncbi.nlm.nih.gov/pubmed/23344005.

(56) References Cited

OTHER PUBLICATIONS

Zhao, D., Banks, S. A., Mitchell, K. H., Lima, D. D. D., Jr, C. W. C., & Fregly, B. J. (2007). Correlation between the Knee Adduction Torque and Medial Contact Force for a Variety of Gait Patterns, (June), 789-797. doi:10.1002/jor.

Zheng, R., Liu, T., Inoue, Y., Shibata, K., & Liu, K. (2008). Kinetics Analysis of Ankle, Knee and Hip Joints Using a Wearable Sensor System. Journal of Biomechanical Science and Engineering, 3(3), 343-355. doi: 1 0.1299/jbse.3.343.

Barrios, J., et al.,. "Gait Retraining to Reduce the Knee Adduction Moment Through Real-Time Visual Feedback of Dynamic Knee Alignment," *J. Biomech*. Author manuscript available in PMC Aug. 10, 2011, pp. 1-16; (published in final form as *Journal of Biomechanics* 43(11), pp. 2208-2213, (2010).).

Hunt, M. et al. "Feasibility of a Gait Retraining Strategy for Reducing Knee Joint Loading: 1-36 Increased Trunk Lean Guided by Real-Time Biofeedback." *Journal of biomechanics* 44.5, pp. 943-947 (2011 ), Abstract only.

International Preliminary Report on Patentability for Int'l Application No. PCT/US2015/027460, filed Apr. 24, 2015, entitled "Feedback Method and Wearable Device to Monitor and Modulate Knee Adduction Moment," dated Nov. 3, 2016.

International Search Report and Written Opinion for Int'l Application No. PCT/US2015/27460, filed Apr. 24, 2015, entitled "Feedback Method and Wearable Device to Monitor and Modulate Knee Adduction Moment," dated Aug. 12, 2015.

Simic, M., et al. "Gait Modification Strategies for Altering Medial Knee Joint Load: A Systematic 1-36 Review," *Arthritis Care & Research* 63.3, pp. 405-426 (2011 ).

Wheeler, J.W., et al. "Real-Time Knee Adduction Moment Feedback for Gait Retraining Through 1-36 Visual and Tactile Displays," *Journal of Biomechanical Engineering* 133.4 (2011).

* cited by examiner

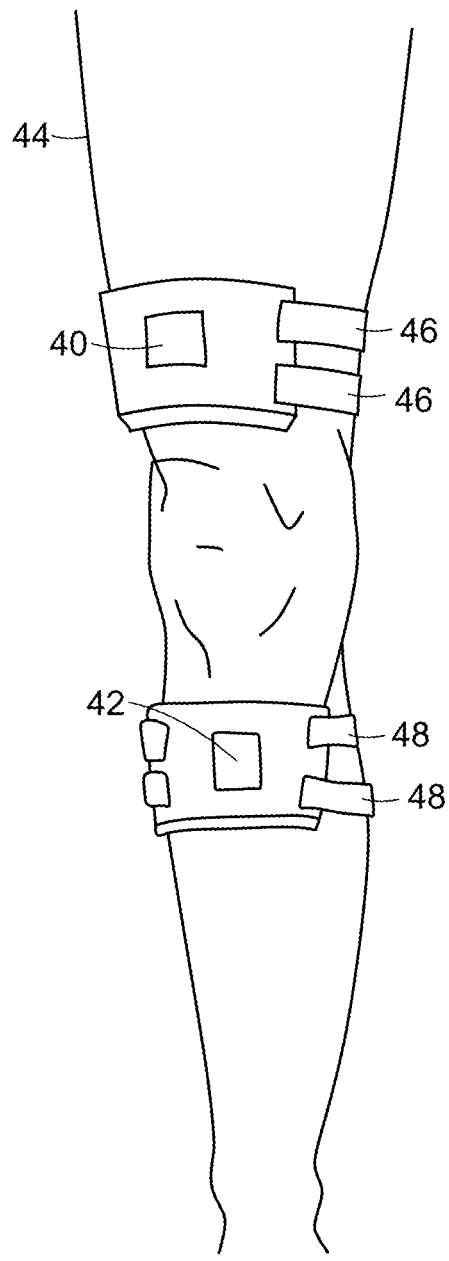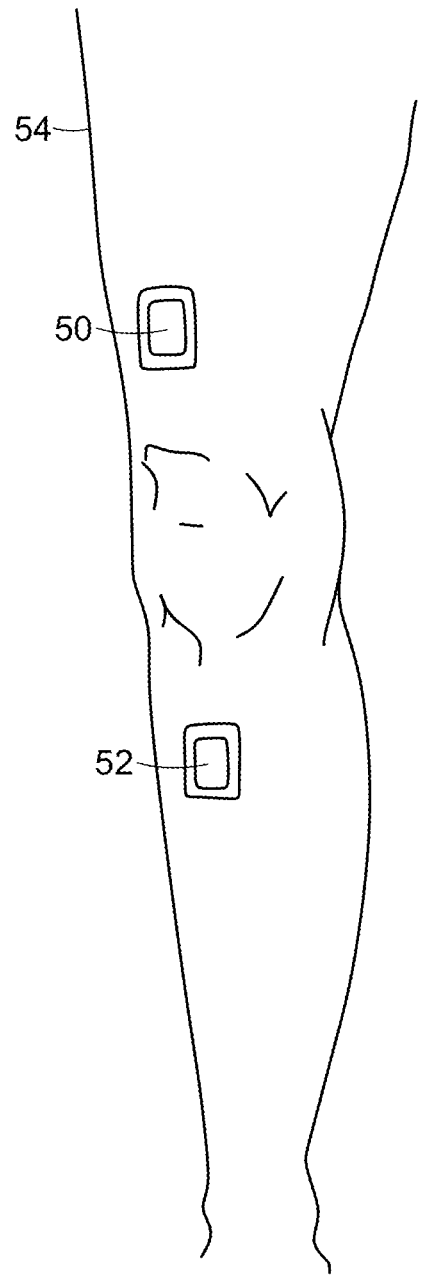
FIG. 3
FIG. 4

FEEDBACK METHOD AND WEARABLE DEVICE TO MONITOR AND MODULATE KNEE ADDUCTION MOMENT

RELATED APPLICATION

This application is the U.S. National Stage of International Application No. PCT/US2015/027460, filed Apr. 24, 2015, which designates the U.S., is published in English, and claims the benefit of U.S. Provisional Application No. 61/984,204, filed on Apr. 25, 2014. The entire teachings of the above applications are incorporated herein by reference.

BACKGROUND OF THE INVENTION

Osteoarthritis (OA) of the knee is a significant public health problem in the United States. An estimated 11 million adults have symptomatic knee osteoarthritis in the U.S. today. (Weinstein et al., 2013). More than a third of these patients have had total knee replacement surgery, and more than half are projected to undergo such surgery during their lifetime. (Weinstein et al., 2013). Osteoarthritic patients in general are more likely to suffer from pain, stiffness, and other discomfort than the non-osteoarthritic population, and to be less physically active (Cook, Pietrobon, & Hegedus, 2007). Elderly knee OA patients with moderate disease progression are moreover less likely to be independent in their daily activities (Guccione, Felson, & Anderson, 1990).

Medial knee osteoarthritis, the most prevalent type of OA, is thought to be exacerbated by high contact force in the medial compartment of the knee. (Jackson, Wluka, Teichtahl, Morris, & Cicuttini, 2004), Measuring this force directly requires implanting a sensor in the knee, but knee adduction moment (KAM) is strongly correlated with medial contact force (Zhao et al., 2007), and is therefore frequently used as a substitute measure. Furthermore, signals related to knee adduction moment, such as mean KAM, first (temporal) peak KAM on each step, and KAM impulse, are variously correlated with disease severity, progression, and symptoms in OA patients (though no study testing whether there is a causal relationship has yet been conducted). (Foroughi, Smith, & Vanwanseele, 2009; Sharma et al., 1998). In light of this information, effort has been put towards developing gait-retraining strategies for lowering knee adduction moment and related signals, in the hope that this can benefit OA patients.

Therefore, a need exists for a feedback method and wearable device to monitor and modulate knee adduction that overcomes or minimizes the above-mentioned deficiencies.

SUMMARY OF THE INVENTION

The invention generally is directed to a method for modulating knee adduction moment of an untethered human during gait, and to a wearable device for modulating knee adduction moment of an untethered human during gait.

In one embodiment, the invention is a method for modulating knee adduction of an untethered human during gait, including the steps of determining at least one feature associated with instantaneous knee adduction moment of the untethered human during a gait cycle, optionally deriving feedback to be transmitted to the human, such as by comparing the at least one feature to a value, such as a target value, and transmitting the feature or feedback to the human for response by the human, thereby modulating knee adduction moment of the untethered human during the gait.

In one embodiment, the method further includes the step of identifying a phase of the untethered human gait cycle associated with the at least one feature. Examples of phases of the untethered human gait cycle include a stance phase and a swing phase of the human gait cycle, or stance phase while the human is being supported by both legs, or stance phase while the human is being supported by only a single leg. In another embodiment, the method further includes the step of identifying a transition condition indicating commencement of a phase of the gait cycle. Examples of transition conditions indicating commencement of a phase of the gait cycle include footstrike and toe off. In one embodiment, the at least one feature of the at least one instantaneous knee adduction moment is determined during a stance phase of the gait cycle. The at least one feature can be determined using, for example, at least one member of the group consisting of center of pressure, ground reaction force, acceleration, tibial orientation, femur orientation and a combination or a derivative thereof.

In certain specific embodiments, the method further includes determining instantaneous knee adduction moment from at least one parameter of the group consisting of center of pressure, ground reaction force, acceleration, tibial orientation, femur orientation and a combination or a derivative thereof. The at least one feature in certain specific embodiments can be, for example, at least one member selected from the group consisting of a peak, a rise-time to a peak, a rate of change, a time between first and second peaks, and impulse associated with instantaneous knee adduction moment. One example of a combination of parameters suitable for use in the present invention includes center of pressure, ground reaction force and tibial orientation. In selected embodiments, the parameter is measured by at least one sensor selected from the group consisting of an accelerometer, a gyroscope, a magnetometer, an optical sensor, an ultrasound transducer or sensor, a pressure sensor and a goniometer. In certain specific embodiments, the method includes the step of employing a sensor fusion algorithm to combine information from a plurality of sensors or sensor types. For example, in one embodiment, a sensor fusion algorithm includes a Kalman filter.

In another embodiment, the instantaneous knee adduction moment is determined from a three-dimensional ground reaction force. In a specific embodiment, the method of the invention further includes the step of estimating a horizontal component of the three-dimensional ground reaction force from a vertical ground reaction force, along with a position of a center of mass with respect to the center of pressure of the untethered human. The position of the center of mass with respect to this inner pressure of the human includes, in one embodiment, a height of the center of mass and a horizontal distance between the center of mass and the center of pressure. The instantaneous knee adduction moment can be calculated by, for example, employing at least one member of the group consisting of tibia length, femur length, hip width, foot length, body height and body weight. In one embodiment, the horizontal component of the three-dimensional ground reaction force is estimated at an angular momentum about the center of mass of the untethered human of about zero during the gait cycle of the untethered human. In one embodiment, the vertical ground reaction force is measured as the weighted sum of pressure measurements from insole sensors. In still another embodiment, the center of mass is estimated as a function of fixed anatomical position. In yet another embodiment, the center of mass is estimated as a function of a fixed periodic trajectory with respect to an anatomical reference point.

In yet another embodiment of the invention, the method further includes the step of determining the relative position of a knee joint center and the center of mass with respect to the center of pressure of the human.

In one embodiment, determining the at least one feature includes the step of measuring a joint angle of the knee joint. In this embodiment the joint angle is measured, in at least one of one, two and three dimensions. The joint angle can be measured, for example, by employing at least one goniometer attached to the knee joint. In another embodiment, determining the at least one feature includes the steps of measuring angular velocity of the knee joint. In yet another embodiment, determining the at least one feature includes the step of determining the position of a knee of the human relative to a center of pressure from relative positions of a tibia and a foot of the human. In one specific embodiment, the relative joint positions are measured, at least in part, by magnetometers mounted on the joints.

In yet another embodiment of the invention, the method includes the further step of attaching tibia and femur inertial measurement units (IMU) to each leg of the individual, and employing the IMUs used to define a tibial IMU frame, a femoral IMU frame and a world frame to thereby obtain the instantaneous knee adduction moment. In yet another embodiment, the method of the invention further includes the step of updating determination of the at least one feature. In one embodiment, the step of determining at least one feature includes determining instantaneous knee adduction moment impulse by integrating the calculated instantaneous knee adduction moment with respect to time over the gait cycle of the untethered human.

In yet another embodiment of the invention, the feedback is transmitted to the human through an interface. In one embodiment, the interface includes at least one member selected from the group consisting of a vibrating motor, an electronic audio assistant, a skin-stretch device, a functional electrical stimulation (FES) device, an orthotic device, a lower limb prosthesis that adapts its shape, behavior or mechanical dynamics to alter knee adduction moment, and a visual display.

In another embodiment, the invention is an autonomous wearable device for modulating knee adduction moment of an untethered human during gait that includes a wearable means for determining at least one feature associated with instantaneous knee adduction moment of the untethered human during a gait cycle, optionally including wearable means for deriving feedback to be transmitted to the human, such as by comparing the least one feature to a value, such as a target value, and wearable means for transmitting the feature or feedback to the human for response by the human, thereby modulating knee adduction moment of the untethered human during the gait.

In yet another embodiment, the invention is an autonomous wearable device for modulating knee adduction moment of an untethered human during gait that includes a tibial sensor, a femoral sensor, an insole sensor, a wearable controller and a wearable feedback system. The wearable controller is electronically linked to the tibial sensor, the femoral sensor and the insole sensor, and is configured to determine at least one feature being associated with instantaneous knee adduction moment calculated from measurements as measured by at least one of the tibial, femoral and insole sensors during a gait cycle of the untethered human. The controller is further optionally configured to derive feedback to be transmitted to the human by, for example, comparing the at least one feature to a value, such as a target value. The wearable feedback system is electronically linked to the wearable controller and is configured to receive the feature, or feedback derived from the feature, from the controller and to transmit the feature or derived feedback to the human for response by the human, to thereby modulate knee adduction moment of the untethered human during the gait. In one embodiment, at least one of the tibial sensor, the femoral sensor and the insole sensor includes at least one member selected from the group consisting of an accelerometer, a gyroscope, a magnetometer, an optical sensor, an ultrasound transistor sensor, a pressure sensor and a goniometer.

The invention provides an autonomous portable, wearable, system for (1) measuring knee adduction moment, and related signals that are correlated with OA progression, in the course of the wearer's daily activities, and (2) conveying information on these measurements to the wearer as he or she walks, and later to his or her clinician as well. Immediate feedback enables patients to adjust their gait and walking speed in response to factors such as, footwear, terrain and fatigue. Furthermore, continuous feedback significantly improves gait over occasional gait-retraining sessions in a clinical environment.

The device of the invention is completely mobile and relatively unencumbering to wear, so that patients may use it in the course of normal daily activities. Measurements can be made using a variety of wearable sensor types. Real-time feedback can be delivered in a variety of ways, and can be functional (e.g. functional electric stimulation of the muscles, actuation of a prosthesis or orthosis, etc.) or merely informative (e.g. a visual display, auditory feedback, vibration of a motor, etc.), or both.

BRIEF DESCRIPTION OF THE DRAWINGS

FIG. 3 is one embodiment of sensors employed by the method and system of the invention, wherein the sensors are strapped to a limb of a user of the invention.

FIG. 4 is an alternative embodiment of sensors employed by the method and system of the invention, wherein the sensors are adhered to a limb of a user of the invention by an adhesive.

DETAILED DESCRIPTION OF THE INVENTION

Figure 1:
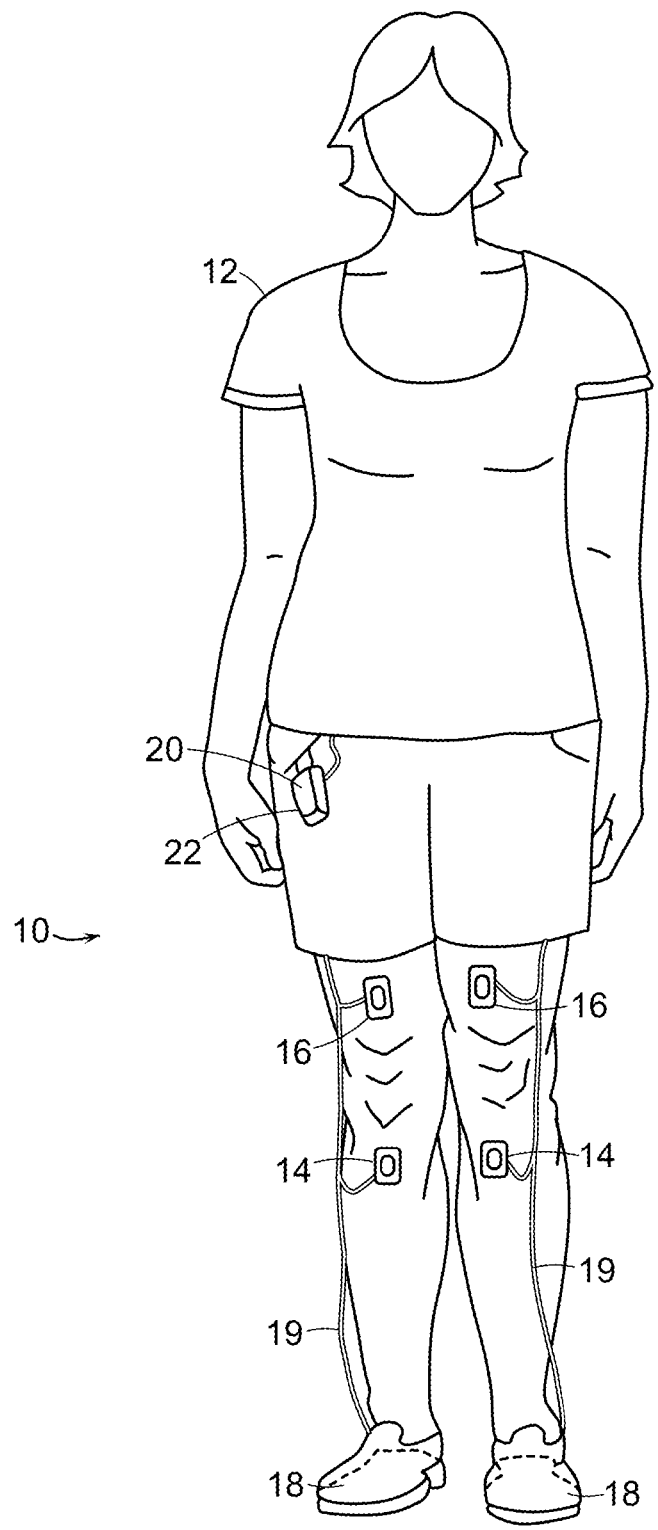
FIG. 1 is a depiction of one embodiment of a wearable system of the invention for modulating knee adduction moment of an untethered human during gait, as worn by a human user.

Generally, the invention is an autonomous wearable device for modulating knee adduction moment of an untethered human during gait that includes a wearable means for determining at least one feature associated with instantaneous knee adduction moment of the untethered human, optional wearable means for determining feedback to be transmitted to the human by, for example, comparing the least one feature to a value, such as a target value, and wearable means for transmitting the feature, or feedback derived from the feature, to the human for response by the human, thereby modulating knee adduction moment of the untethered human during the gait. An "untethered human," as defined herein, is a human that is not physically connected to a device that determines features or derives feedback associated with gait of the human and is stationary, or not autonomous or wearable, thereby limiting mobility of the human during the gait.

In yet another embodiment, the invention is an autonomous wearable device for modulating knee adduction moment of an untethered human during gait that includes a tibial sensor, a femoral sensor, an insole sensor, a wearable controller and a wearable feedback system. The wearable controller is electronically linked to the tibial sensor, the femoral sensor and the insole sensor, and is configured to determine at least one feature associated with instantaneous knee adduction moment or a parameter of the instantaneous knee adduction moment measured by at least one of the tibial, femoral and insole sensors, the parameter being associated with a phase of gait of the untethered human. The controller can be further configured to derive feedback to be transmitted to the human by, for example, comparing the at least one feature to a value, such as a target value. The wearable feedback system is electronically linked to the wearable controller and is configured to receive the calculated feedback from the controller and to transmit the feature, or feedback derived from the feature, to the human for response by humans to thereby modulate knee adduction moment of the untethered human during the gait. In one embodiment, at least one of the tibial sensor, the femoral sensor and the insole sensor includes at least one member selected from the group consisting of an accelerometer, a gyroscope, a magnetometer, an optical sensor, an ultrasound transistor sensor, a pressure sensor and a goniometer.

In one embodiment, the invention is a fully-mobile, wearable system that both measures knee adduction moment and provides real-time feedback to the wearer. The system includes, for example, (1) a set of sensors to measure signals needed to estimate knee adduction moment; (2) a feedback transmission subsystem such as an actuator, mobile computer and application, speaker, or voltage or current source; (3) a power source such as a battery; (4) a set of microprocessors that receive data from the sensors, calculate knee adduction moment, deliver commands to the feedback transmission system, and handle startup, shutdown, power management, data logging, and fault recovery (5) wired or wireless connections for communication and power transmission between the components; (6) straps to attach the system to the body; and (7) a user interface.

FIG. 1 is a block diagram of one embodiment of a wearable device of the invention. As shown in FIG. 1, wearable system 10 of the invention is worn by human 12. Wearable system 10 includes tibial sensor 14 at a tibia of human 12, femoral sensor 16 at a femur of human 12, insole sensor 18 at an insole of human 12, wearable controller 20 worn by human 12 and electronically linked, for example, via cable 19, to tibial sensor 14, femoral sensor 16 and insole sensor 18, and wearable feedback system 22 worn by human 12, such as at wearable controller 20, and electronically linked to wearable controller 20. As illustrated in FIG. 1, at least one sensor of each of sensors 14, 16 and 18 can be placed on each leg of human 12. Controller 20 calculates instantaneous knee adduction moment based on at least one parameter measured by at least one of tibial sensor 14, femoral sensor 16 and insole sensor 18, the parameter being associated with a state condition of an independent human gait cycle. Wearable controller 20 further calculates feedback from the instantaneous knee adduction moment and the at least one parameter measured, wearable feedback system 22 receives the feedback from wearable controller 20 and transmits the feedback to human 12. In at least one embodiment, at least one of tibial sensor 14, femoral sensor 16 and insole sensor 18 includes at least one member selected from the group consisting of an accelerator, a gyroscope, a magnetometer, an optical sensor, an ultrasound transistor sensor, a pressure sensor and a goniometer.

Figure 2:
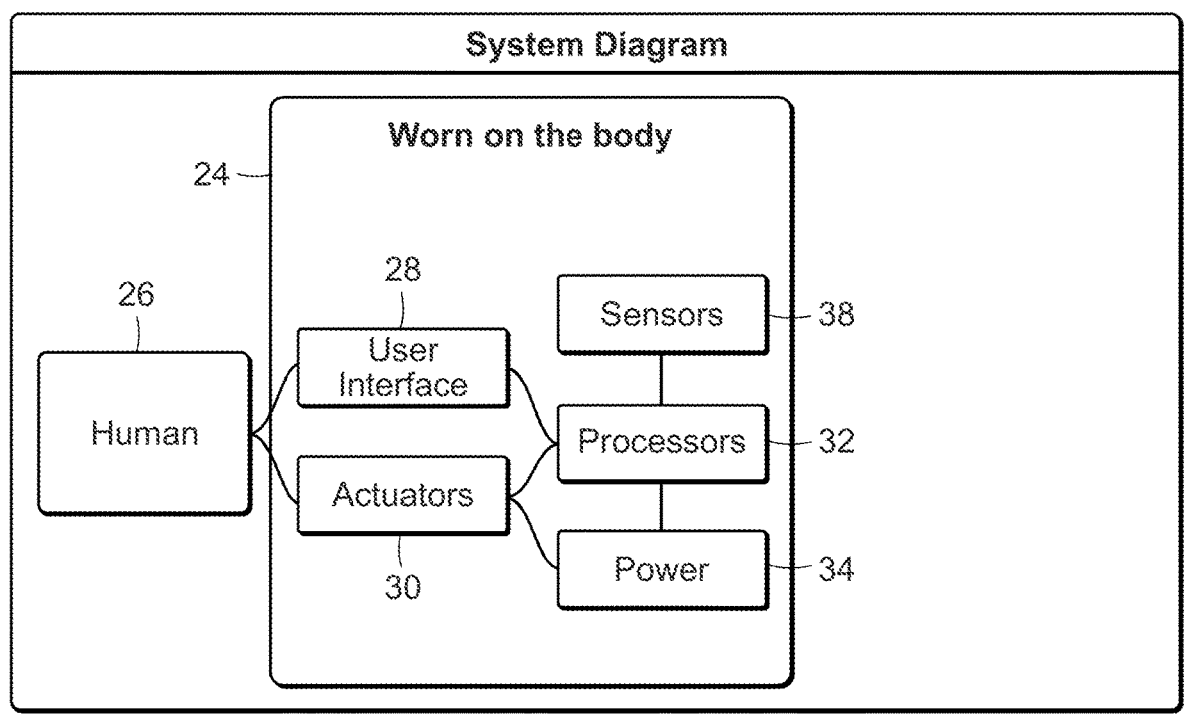
FIG. 2 is a schematic representation of one embodiment of a wearable system of the invention for modulating knee adduction moment of the untethered human during gait.

A schematic representation of one embodiment of a wearable device of the invention is shown in FIG. 2. As shown therein, wearable system 24 is worn on human 26. Wearable system 24 includes use interface 28 and actuators 30 in communication with human 26. User interface 28 and actuators 30 are controlled by processors 32. Power source 34 supports processors 36 and actuators 30. Processors 36 are also in communication with sensors 38, such as the sensors discussed above.

In another embodiment, the invention is a method for estimating ground reaction forces in three dimensions from pressure insole data in real time. In one specific embodiment, the method does not require calibration with any other equipment such as forceplates or motion capture systems, based on the assumption that the body's total angular momentum is approximately zero during steady-state walking.

System Description

Terminology

Knee adduction moment is the moment about the center of the knee joint in the coronal plane, defined anatomically in this case as the plane perpendicular to the flexion/extension axis of the knee, and passing through the center of the knee joint. It can be calculated as the cross-product of the component of the ground reaction force on the body in the coronal plane with the knee adduction moment arm. The knee adduction moment arm is the vector from the knee joint center to the line passing through the body's center of pressure and pointing in the direction of the ground reaction force.

Knee adduction moment impulse is computed by integrating knee adduction moment with respect to time over each gait cycle.

Calculating knee adduction moment requires both kinematic and force measurements.

Overview of Components

A set of sensors is used to track the relative orientations and positions of segments of the tibias and femurs, and derivatives of these orientations and positions (angular and translational velocity, angular and translational acceleration, etc.). Any sensors or combinations of sensors capable of providing information towards these measurements may be used, as long as they are portable; examples include but are not limited to accelerometers, gyroscopes, magnetometers, optical sensors, ultrasound transmitters/sensors, and goniometers. Sensor fusion algorithms, such as the often-used Kalman filter (Kalman 1960), may be used as part of the calculation process in order to combine information from multiple sensors and from heterogeneous sensor types.

Such measurements may also be combined with dimensions of the user's body, perhaps including, for instance, tibia length, femur length, hip width, foot length, and body height and weight. These dimensions may be measured and given as inputs to the device through the user interface, or they may be estimated based on average measurements from a population representative of the user.

A sensor or set of sensors are used to measure the three-dimensional magnitude and orientation of the ground reaction force exerted on the body as well as the location of the center of pressure (the point on the ground at which the ground reaction force is exerted). These systems may include, for instance, force transducers and pressure-sensing insoles.

In the case where a pressure insole—or any sensor capable of measuring only vertical ground reaction force—is used, the horizontal component of ground reaction force must be estimated. In one embodiment of the invention, horizontal ground reaction force is estimated using only (1) vertical ground reaction force (2) the position of the body's center of mass with respect to the center of pressure, based on the simplifying assumption that the body's angular momentum about its center of mass is approximately zero during walking, as hypothesized and supported by Herr and Popovic (Herr & Popovic, 2008), the teachings of which are incorporated by reference in its entirety.

The above sensors communicate with one or several microprocessors. The function of these processors may include, for instance: reading and filtering sensor data, loading stored information about the user, calculating any signals of interest including knee adduction moment, storing raw or processed data for later analysis, communicating with feedback elements, communicating with the user interface, and managing system power.

Feedback elements may include, for instance: vibrating motors placed near the skin, so that the user can feel them buzz; a speaker or electronic audio system, to makes sounds which the user can hear; a skin stretch device, which communicates information to the user by gently stretching a small area of skin on, for instance, the lower back; an orthotic device worn on the leg, which may apply forces to the body, altering knee adduction moment; a lower-limb prosthesis capable of adapting its shape, behavior or mechanical dynamics in a way that alters knee adduction moment; and a visual display of data, created by software running on a portable electronic device such as a smartphone or tablet.

A battery or set of batteries powers elements of the system requiring electricity.

A user interface allows the user to calibrate the system, turn it off and on and to control certain aspects of its behavior. This interface may include: an on/off switch; a volume or amplitude knob for auditory or tactile feedback, in case the user finds the volume or amplitude of the feedback to be generally too high or too low; and a piece of software running on a device (preferably portable, such as a smartphone or tablet) allowing the user to calibrate the device with, for instance, physical information such as body measurements, and possibly to select different modes of feedback or change parameters related to that feedback. This user interface may be part of the software used to present visual feedback.

All elements of the system are attached to the user's body, or portable in a hand or pocket, so that the entire system is mobile. Attachments should be comfortable to wear while walking, and allow the user to easily turn the system on and off and adjust parameters such as feedback mode as necessary while walking. In the case of sensors which must be fixed at a constant anatomical location, such as for instance an IMU on the knee, attachments should prevent these sensors from sliding, twisting, or coming off of the body. Attachments should interfere as little as possible with movement and clothing.

In addition to real-time feedback, the system may include software allowing the user or a clinician to review past data.

Attachments

A subsystem of this invention for attaching sensors to the body makes placement of the sensors automatic and repeatable, so that users consistently attach sensors to the body in the right locations with ease. For instance, in the case of the embodiment of the kinematic measurement system described below, comprised of a femoral and tibia IMU on each leg, the attachment system can indicate to the user when the sensor is properly aligned with the bone beneath it. Furthermore, the attachment system can prevent sensors from moving relative to their anatomical reference points during physical activity, to minimize error due to sensor movement, and reduce the need for recalibration. The attachment subsystem is comfortable, easy to wear under clothing, and lightweight. Two possible embodiments of the attachment subsystems are shown in FIGS. 3-6B.

Figure 5:
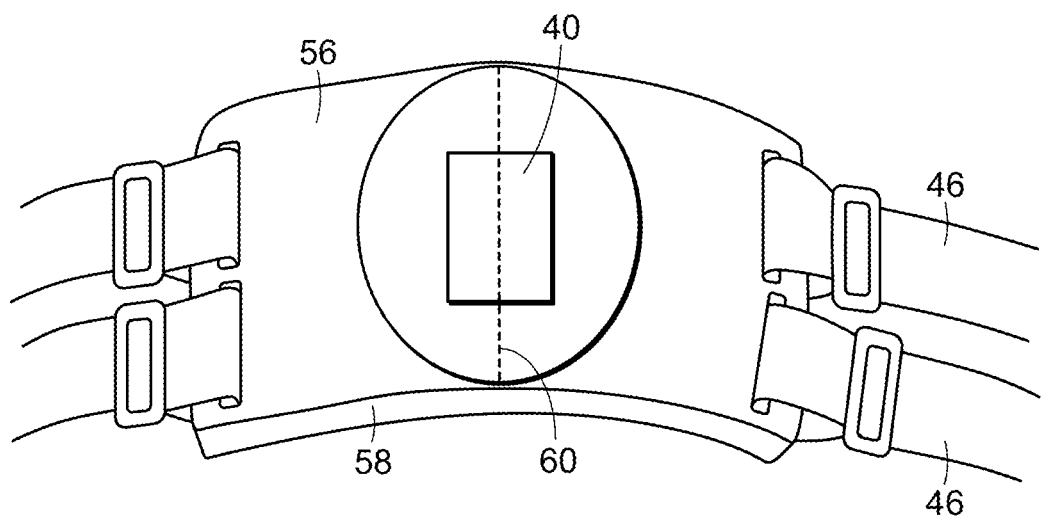
FIG. 5 is a more detailed representation of the embodiment shown in FIG. 3.

As shown in FIG. 3, sensors 40, 42 are attached to body 44 using straps 46, 48 respectively. As shown in FIG. 5 sensor 40 can be attached to, for example, flexible outer shell 56, with semi-adhesive padding 58 between the shell and the body for comfort and to reduce motion of the sensor relative to the body. Straps 46, 48 are fastened around limb 44 to keep sensors 40, 42 in place. A line 60 is a coordinate axis of sensor 40, that enables the user to align sensor 40 with an anatomical feature, such as the long axis of the tibia or femur of limb 44. Sensors 40, 42, themselves (and their respective coordinate axis) may be free to rotate with respect to the rest of the attachment system, so that anatomical alignment may be achieved more easily without adjusting the orientation of sensors 40, 42.

Figure 6A:
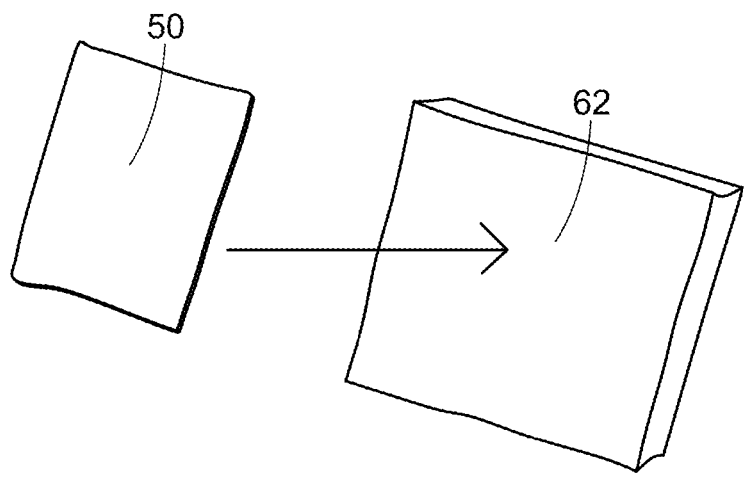
FIGS. 6A and 6B are more detailed representations of the embodiment shown in FIG. 4.
Figure 6B:
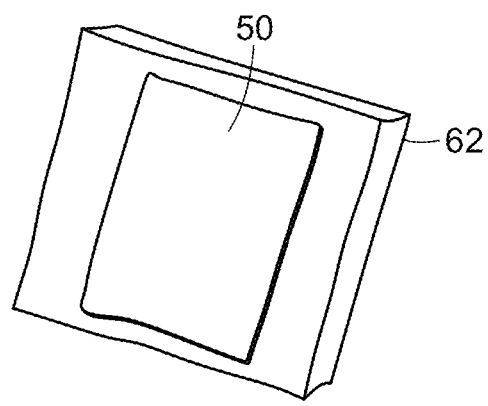

In an alternative embodiment, shown in FIG. 4 and FIGS. 6A and 6B, sensors 50, 52 are attached directly to skin of limb 44 using a suitable adhesive, thereby eliminating straps 46, 48 of FIGS. 3 and 4. An appropriate adhesive would be any that is relatively secure, safe for prolonged contact with skin, and easy to remove without pain or residue on the skin.

Gel pads can be used for attaching surface electrodes to the body as an example of such an adhesive. Adhesive 62 may be disposable, even if the sensors themselves are not.

Force Measurements

In one embodiment, a force-instrumented shoe is employed to measure three-dimensional ground reaction forces and center of pressure locations at each foot, in the manner described, for example in Bae et al., 2011, Liedtke et al., 2007 and Liu et al., 2010, the relevant teachings of all of which are incorporated by reference in their entirety.

In another embodiment, three-dimensional ground reaction forces are estimated using a pressure-sensing insole (which can measure center of pressure location, as well as vertical—but not horizontal—ground reaction force at each foot) along with kinematic data, such as described by Rouhani et al., 2010, Forner Cordero et al., 2004, and Fong et al., 2008, the relevant teachings of all of which are incorporated herein by reference in their entirety. In still another embodiment of the invention, horizontal ground reaction forces are estimated by meeting the simplifying assumption that angular momentum about the center of mass of the body remains close to zero throughout the gait cycle, as hypothesized and supported by Herr & Popovic, 2008, the relevant teachings of which are incorporated herein by reference in their entirety. Under this assumption, the horizontal component of the ground reaction force is a function of (1) the vertical ground reaction force, which can be measured from the insoles (2) the height of the center of mass and (3) the horizontal distance between center of mass and center of pressure. (The last two parameters require information about the relative position of the center of mass—as described infra.)

In one embodiment, three-dimensional ground reaction forces are estimated using vertical ground reaction force, center of pressure location and kinematic data as follows:

$$F_x = \frac{F_z}{z_{com}} * (x_{com} - x_{cop}), \text{ where}$$

$F_x$ is ground reaction force in the coronal plane $F_z$ is vertical ground reaction force $z_{com}$ is the height of the center of mass $x_{com}$ is the mediolateral position of the center of mass $x_{cop}$ is the mediolateral position of the center of pressure Likewise $$F_y = \frac{F_z}{z_{com}} * (y_{com} - y_{cop})$$

$F_y$ is a ground reaction force in the sagittal plane. $F_x$, $F_y$ and $F_z$ are all orthogonal to each other.

As is well-known, the location of the center of pressure may be obtained from pressure-sensing insole measurements as follows. The center of pressure during double stance (both feet on the ground) is the average position of the centers of pressure at each foot, weighted by the magnitude of the vertical ground reaction forces on each foot.

$$x_{cop} = \frac{F_{z,1}}{F_{z,1} + F_{z,2}} * (x_{cop,1}) + \frac{F_{z,2}}{F_{z,1} + F_{z,2}} * (x_{cop,2}), \text{ and}$$

$$y_{cop} = \frac{F_{z,1}}{F_{z,1} + F_{z,2}} * (y_{cop,1}) + \frac{F_{z,2}}{F_{z,1} + F_{z,2}} * (y_{cop,2}), \text{ where}$$

$x_{cop}$ is the mediolateral position of the center of pressure $y_{cop}$ is the anterior/posterior position of the center of pressure $x_{cop,i}$ is the mediolateral position of the center of pressure at foot $i$ (1 or 2)

$y_{cop,i}$ is the anterior/posterior position of the center of pressure at foot $i$ $F_{z,i}$ is vertical ground reaction force at foot $i$ Methods of calculating center of pressure position from pressure-sensing insole readings are known. The insole provides an array of vertical pressure measurements evenly-distributed across the sole of the foot. The mean position of the sensors, weighted by the magnitude of the pressure measurement at each sensor, gives the location of the center of pressure for that foot. (Han, Paik, & Im, 1999), the relevant teachings of which are incorporated herein by reference in their entirety. For any (two-dimensional) coordinate frame in which the position (x, y) and pressure P at each of N sensors are known for the ith foot:

$$x_{cop,i} = \frac{\sum_{j=1}^{N} P_{i,j} * x_{i,j}}{\sum_{j=1}^{N} P_{i,j}}$$

$$y_{cop,i} = \frac{\sum_{j=1}^{N} P_{i,j} * y_{i,j}}{\sum_{j=1}^{N} P_{i,j}}$$

Measurement of vertical ground reaction force at each foot ($F_{z,i}$) can be obtained from a pressure sensing insole as the sum of pressure measurements from the insole sensors, weighted by the area of each cell:

$$F_{z,i} = \sum_{j=1}^{N} P_{i,j} * \text{Cell Area}_{i,j}$$

It is not necessary that the insole use an array of pressure sensors. A flat insole capable of calculating vertical ground reaction force and center of pressure location on the sole of the foot is suitable.

Kinematic Measurements

Figure 7:
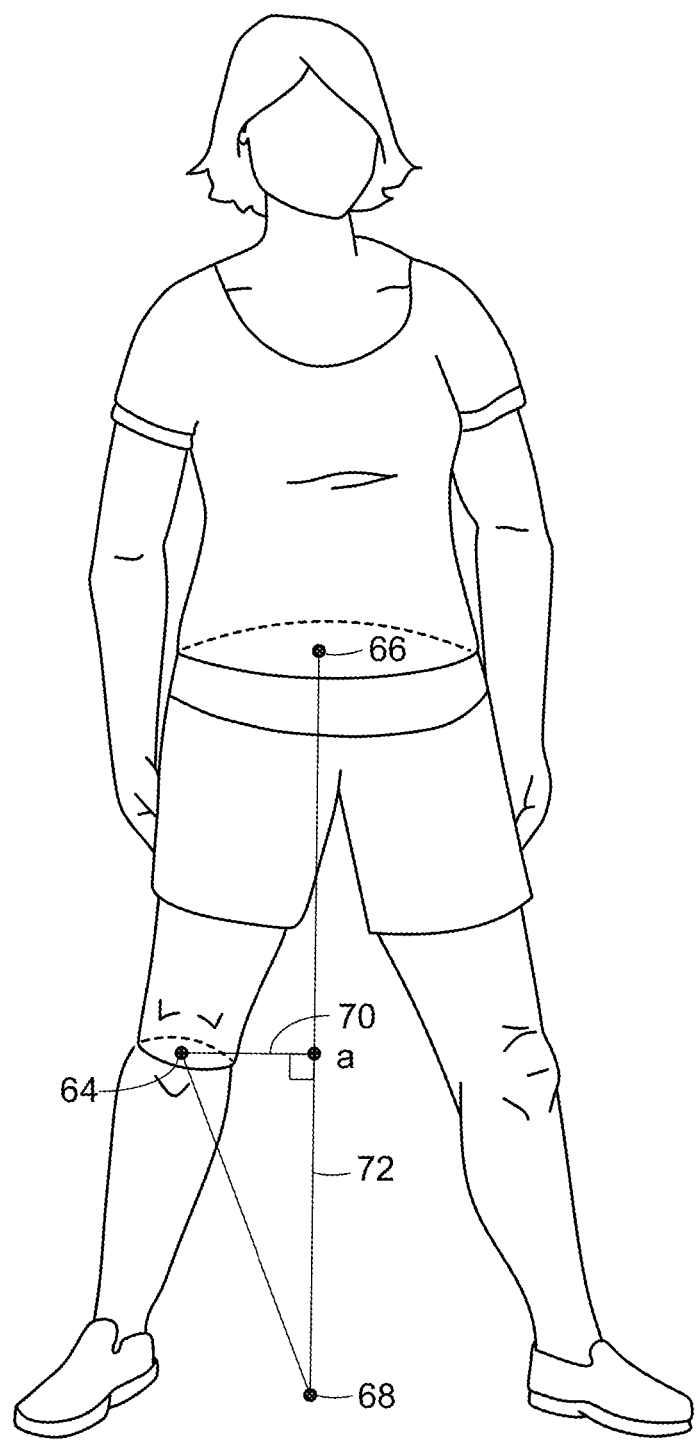
FIG. 7 is a representation of knee adduction moment of a human user.

In one embodiment, the invention includes portable sensors that measure relative position, shown in FIG. 7, of (1) a knee joint center 64, and (2) calculates or estimates the center of mass (com) 66, with respect to a center of pressure (COP). With this information, a knee adduction moment arm can be calculated as a vector 70 from knee-joint center 64 to a line 72 from center of pressure 68 to center of mass 66.

For any type of sensor, sensor readings may be interpreted in the world frame based on (1) information about the way in which the sensor is attached to the body (e.g., a goniometer measuring the angle of flexion or extension of the knee may be attached so that it measures primarily this angle, with its vertex collinear with knee joint center 64 along the axis of flexion), assumptions about the mechanics of the body (e.g., that the ankle may be modeled as a pin joint, having only one axis of rotation), and information about fixed body segment lengths (e.g., the distance between the ankle and knee joint centers along the tibia), lengths which may either be estimated, or manually measured by the user and used to calibrate the device. Or, as an alternative to measuring or estimating perpendicular distances from sensors to the bones below, ultrasound could be used to measure bone depth, as described, for example, in U.S. Pat. No. 7,481,780, the relevant teachings of which are incorporated by reference in its entirety.

In one embodiment of a kinematic measurement system, joint angles are measured in between one and three dimensions at each joint using goniometers attached to the joints.

In another embodiment, relative joint positions may be measured using magnetometers mounted on the joints.

In another embodiment of a kinematic measurement system, inertial sensors are mounted on the joints so as to measure acceleration, obtaining position by integration from known or estimated initial conditions. To reduce drift, other sensors may be added, as is often accomplished using IMUs (inertial measurement units), which make use of gyroscopes to measure angular velocity and thereby improve location estimation accuracy.

In a further refinement of the above embodiment, two IMUs are attached to each leg. One IMU (with three-axis accelerometers and gyroscopes) is attached to the anterior side of the leg above the tibia, and another to the anterior side of the leg above the femur, as, for example, illustrated for sensors 14 and 16 in FIG. 1, sensors 40 and 42 in FIG. 3, and sensors 50 and 52 in FIG. 4. A linked-segment model is assumed, with pinjoint hips and ankles, and with ball-joint knees. Three reference frames on each leg are defined: the tibial IMU frame, the femoral IMU frame, and the world frame. The world frame has its origin on the ground, at the location of the back of the heel while the foot is on the ground; the z-axis is defined as being parallel to the direction of gravity (assumed perpendicular to the ground); the x-axis is defined as being parallel to the sagittal plane (assumed perpendicular to gravity). The coordinate axes of the tibial and femoral IMU's are those defined by the sensors own internal coordinate frames. The tibial IMU is attached to the body in such a way that one axis (defined as the z-axis) is parallel to the tibial axis. The femoral IMU is attached to the body in such a way that one axis (defined as the z-axis) is parallel to the femoral axis, and so that another axis (defined as the x-axis) is parallel to the sagittal plane.

The system can be calibrated, for example, with information about the geometry of the user's body and the position of the sensors on the body. The joint centers of the knee and hip lie at a constant position in the coordinate frame of the femoral IMU, while the joint centers of the knee and ankle lie at a constant position in the coordinate frame of the tibial IMU, under the assumption that the sensor is relatively rigidly attached to the bone. These joint center positions may be calculated by the user (or another person) by measuring distances from the IMUs to certain anatomical markers, following instructions provided with the device. The distance from one hip joint center to the other in the coronal plane may likewise be measured and used to calibrate the device.

Figure 8:
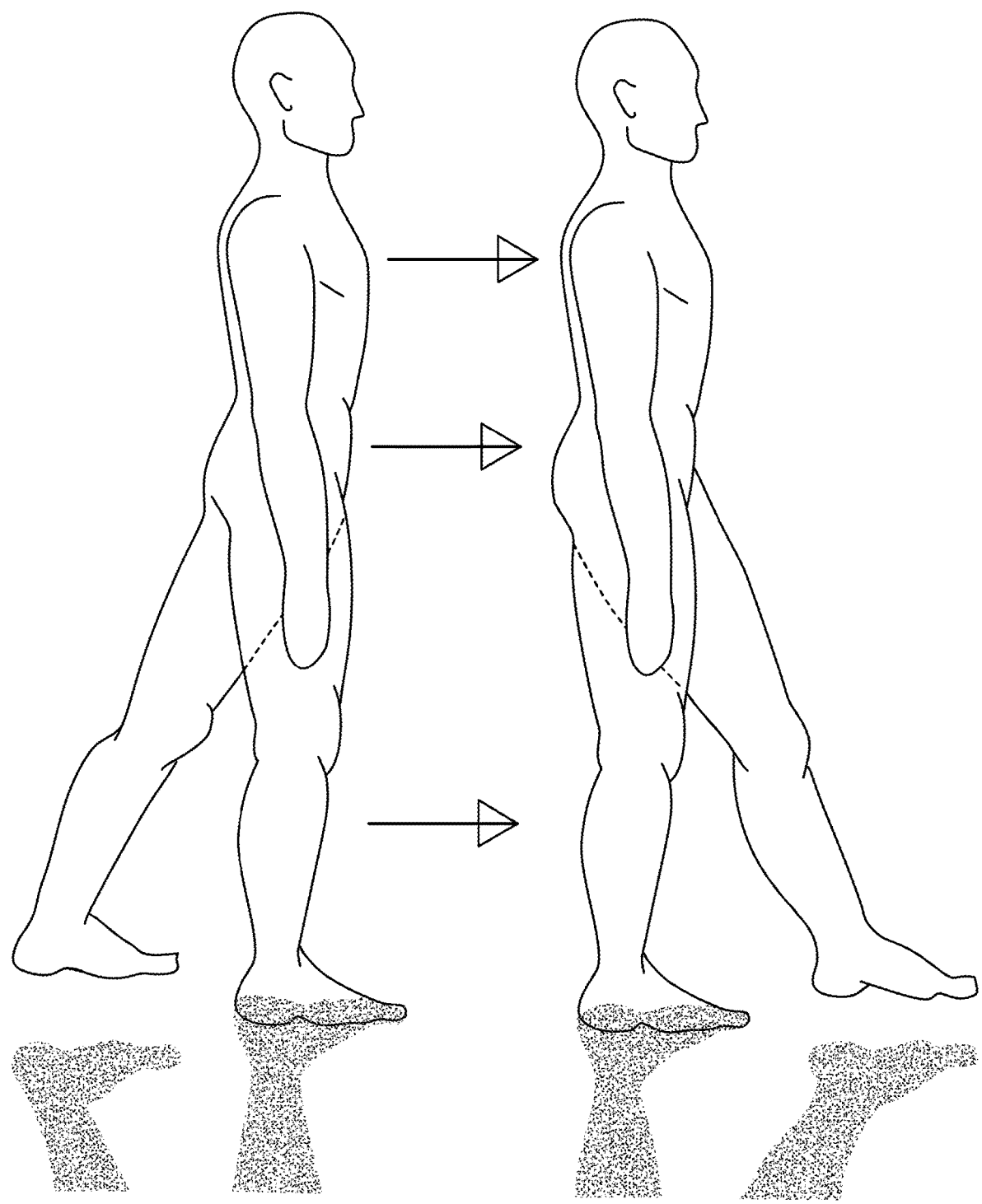
FIG. 8 is a schematic representation of one embodiment of the calibration motion employed by the method and wearable device of the invention.

Gait kinematics can be measured, for example, in real time by integration of IMU readings, starting from known initial conditions, as is well-established in the field. Initial conditions for this system may be obtained, for instance, as follows: with the subject standing still in a neutral pose (e.g., with heels roughly below hips and feet pointing roughly forward), the orientations of the two IMUs on a single leg are known in the world frame in two dimensions (pitch and roll) based on the difference between their accelerometer readings, which represent the direction of gravity since the user is stationary. The yaw orientation of the femoral IMU is further known (in the world frame) since its x-axis is known to be parallel to the sagittal plane; thus the orientation of the femoral IMU's coordinate axes in the world frame is known. The yaw orientation of the tibial IMU may then be estimated via calibration motions. For example, the user may lift the toe slightly off the ground and slowly swing the entire leg, with the knee locked, back and forth parallel to the sagittal plane as can be seen in FIG. 8. This establishes the orientation of the world-frame sagittal plane in the tibial IMU's coordinate frame, and hence the orientation of the tibial IMU's coordinate frame with respect to the world frame is known.

Figure 9:
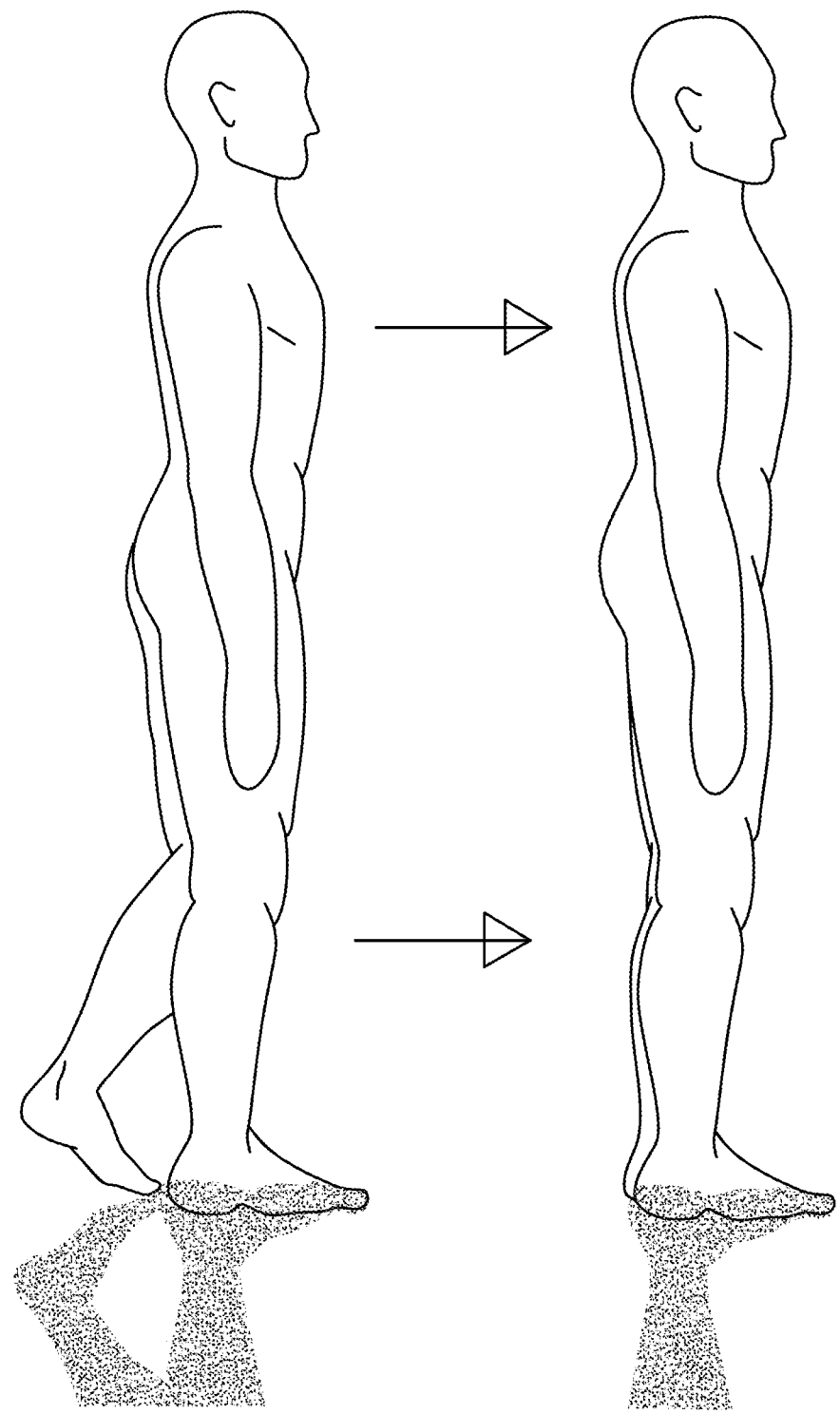
FIG. 9 is another embodiment of a representation of calibration motion employed by the method and wearable system of the invention.

Further, the axis of flexion and extension of the knee may be calculated in the tibia IMU coordinate frame by the user's slowly flexing and extending the tibia while the femur is held stationary in a neutral position, as can be seen from FIG. 9. The axis about which the tibia rotates (as measured by the tibia IMU and converted to world-frame coordinates) is the axis of flexion and extension of the knee.

The coordinate transformation between the two IMU's coordinate frames with the body in a neutral pose (which may be assumed to be the same as the rotational transformation between the two IMUs during the full-leg-swing calibration motion) may thus be obtained, since the rotational transformation from each IMU's coordinate frame to the world frame is known, and since the position of the knee joint center in both the tibia IMU and the femoral IMU coordinate frames is known. Additionally, since each IMU's initial (neutral-pose) orientation with respect to the world frame is known, the orientations of both the tibia and the femur are also known in the world frame; likewise are the positions of the knee, hip, and ankle joints (relative to the other joints on that leg). Hence, starting from a resting pose, the system may track knee, hip, and ankle joint position with respect to the initial position of, for instance, the ankle.

To determine the relative positions of joints not on the same leg in the initial neutral pose, it may be continued to be assumed that the axis defined by the two hip joint centers is perpendicular to the sagittal plane and parallel to the axial plane. With this assumption, the position of either hip joint center with respect to the other is known in the world frame, and therefore, the position of any of the relevant joints relative to any other is fully-defined in the world frame in the initial neutral pose, and can be subsequently be obtained by integration.

The position of the center of mass can be estimated in a variety of ways. For instance, the center of mass can be considered to have a fixed anatomical position, such as the pelvic center. In this case, the information above is sufficient to calculate the position of the center of mass in the world frame based on an estimate of the average position of the anatomical reference point with respect to the hip joint centers. Additional information, such as the height of the user, may improve the estimate based on population averages of center of mass height as a percentage of body height. In an alternate example, the position of the center of mass may be estimated to follow a fixed periodic trajectory with respect to an anatomical reference point, as suggested by Minetti et al. (Minetti, Cisotti & Mian, 2011), the relevant teachings of which are incorporated herein in their entirety).

It will be observed that additional IMUs or other sensors can be added to improve estimates. Integration error can be limited with commonly-used techniques; for instance, if an IMU is placed on the foot, a zero-velocity update algorithm may be applicable.

Also, while the language used here has referred to biological legs, it will be seen that the same technology and calibration process could be applied in the case of an amputee.

Processor

Method

Generally, the invention is a method for modulating knee adduction of an untethered human during gait, including the steps of determining at least one feature associated with instantaneous knee adduction moment of the untethered human of a gait cycle, optionally deriving feedback to be transmitted to the human by, for example, comparing the at least one feature to a value such as a target value, and transmitting the feature, or feedback derived from the feature, to the human for response by the human, thereby modulating knee adduction moment of the untethered human during the gait.

In one embodiment, the method further includes the step of identifying a phase of the untethered human gait cycle associated with the at least one feature. Examples of phases of the untethered human gait cycle include a stance phase and a swing phase of the human gait cycle, or a stance phase while the human is being supported by both legs, or stance phase while the human is being supported by only a single leg. In another embodiment, the method further includes the step of identifying a transition condition indicating commencement of the phase. Examples of transition conditions indicating commencement of a phase of the gait cycle include foot-strike and toe-off. In one embodiment, the at least one feature of the at least one instantaneous knee adduction moment is determined during a stance phase of the gait. The at least one feature can be determined using, for example, at least one member of the group consisting of center of pressure, ground reaction force, acceleration, tibial orientation, femur orientation and a combination or a derivative thereof.

In certain specific embodiments, the instantaneous knee adduction moment is determined from at least one parameter selected from the group consisting of center of pressure, ground reaction force, acceleration, tibial orientation, femur orientation and a combination or a derivative thereof. The at least one feature in certain specific embodiments can be, for example, at least one member selected from the group consisting of a peak, a rise-time to a peak, a rate of change, a time between first and second peaks, and impulse of the instantaneous knee adduction moment. One example of a combination of parameters suitable for use in the present invention includes center of pressure, ground reaction force and tibial orientation. In selected embodiments, the parameter is measured by at least one sensor selected from the group consisting of an accelerometer, a gyroscope, a magnetometer, an optical sensor, an ultrasound transducer or sensor, a pressure sensor and a goniometer. In certain specific embodiments, the method includes the step of employing a sensor fusion algorithm to combine information from a plurality of sensors or sensor types. For example, in one embodiment, a sensor fusion algorithm includes a Kalman filter.

In another embodiment, the instantaneous knee adduction moment is determined from a three-dimensional ground reaction force. In a specific embodiment, the method of the invention further includes the step of estimating a horizontal component of the three-dimensional ground reaction force from a vertical ground reaction force, along with a position of a center of mass with respect to the center of pressure of the untethered human. The position of the center of mass with respect to this inner pressure of the human includes, in one embodiment, a height of the center of mass and a horizontal distance between the center of mass and the center of pressure. The instantaneous knee adduction moment can be calculated by, for example, employing at least one member of the group consisting of tibia length, femur length, hip width, foot length, body height and body weight. In one embodiment, the horizontal component of the three-dimensional ground reaction force is estimated at an angular momentum about the center of mass of the untethered human of about zero during the gait cycle of the untethered human. In one embodiment, the vertical ground reaction force is measured as the weighted sum of pressure measurements from insole sensors. In still another embodiment, the center of mass is estimated as a function of fixed anatomical position. In yet another embodiment, the center of mass is estimated as a function of a fixed periodic trajectory with respect to an anatomical reference point.

In yet another embodiment of the invention, the method further includes the step of determining the relative position of being a knee joint center and the center of mass with respect to the center of pressure of the human.

In one embodiment, determining at least one feature includes the step of measuring a joint angle of the knee joint. In this embodiment the joint angle is measured, in at least one of one, two and three dimensions. The joint angle can be measured, for example, by employing at least one goniometer attached to the knee joint. In another embodiment, determining the at least one feature includes the steps of measuring angular velocity of the knee joint. In yet another embodiment, determining at least one feature includes the step of determining the position of a knee of the human relative to a center of pressure from relative positions of a tibia and a foot of the human. In one specific embodiment, the relative joint positions are measured, at least in part, by magnetometers mounted on the joints.

In yet another embodiment of the invention, the method includes the further step of attaching tibia and femur inertial measurement units (IMU) to each leg of the individual, and employing the IMUs used to define a tibial IMU frame, a femoral IMU frame and a world frame to thereby obtain the instantaneous knee adduction moment. In yet another embodiment, the method of the invention further includes the step of updating determination of the at least one feature. In one embodiment, the step of determining at least one feature includes determining instantaneous knee adduction moment impulse by integrating an instantaneous knee adduction moment with respect to time over the gait cycle of the untethered human.

In yet another embodiment of the invention, the feedback is transmitted to the human through an interface. In one embodiment, the interface includes at least one member selected from the group consisting of a vibrating motor, an electronic audio assistant, a skin-stretch device, a functional electrical stimulation (FES) device, an orthotic device, a lower limb prosthesis that adapts its shape, behavior or mechanical dynamics to alter knee adduction moment, and a visual display.

Figure 10:
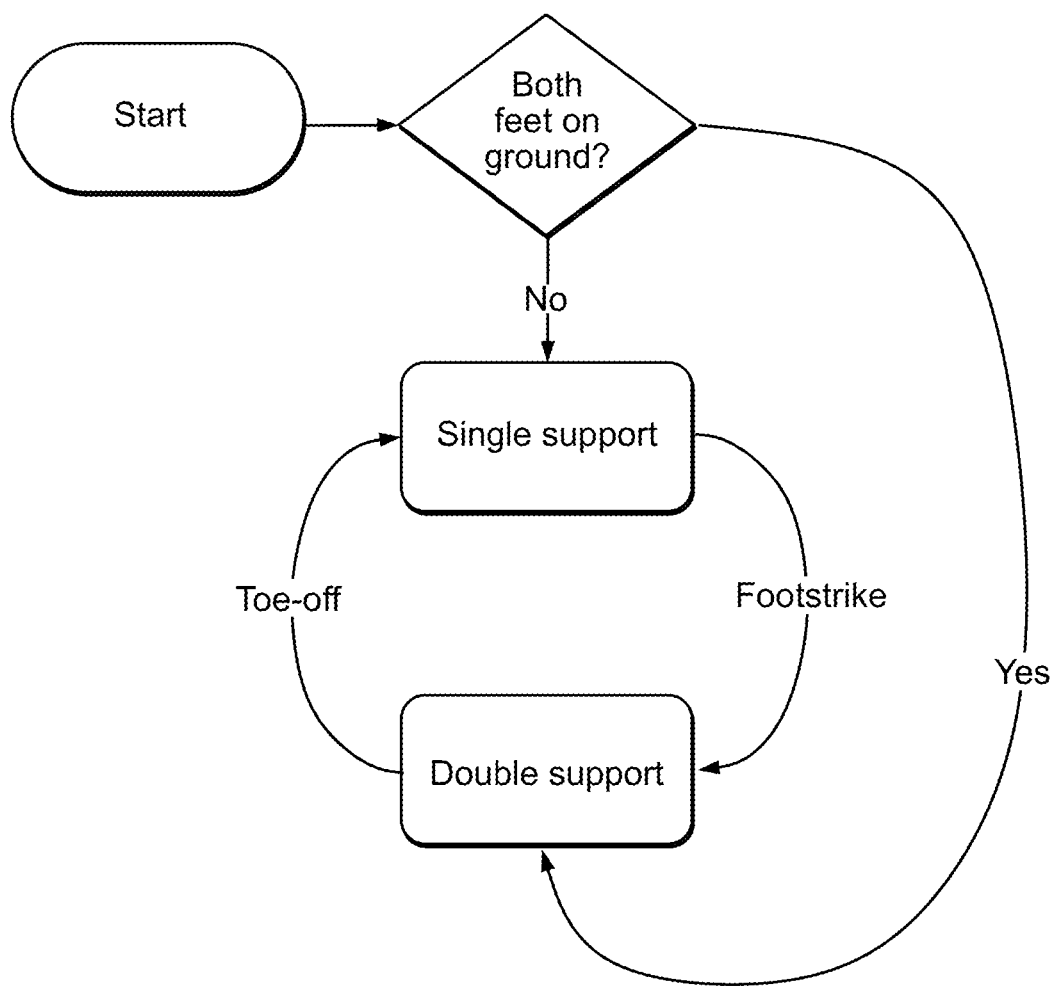
FIG. 10 is a schematic representation of one embodiment of a method of the invention.

As can be seen in FIG. 10, one embodiment of this invention is a method that can be represented as a state machine having a main loop of two states, namely single and double support. The states can be, but need not be, at least a portion of at least one phase of a human gait cycle. An example of a suitable phase of the human gait cycle for application of the invention is a stance phase. Knee adduction moment is calculated for both knees during double support, and for the stance leg during single support. In both states, the main loop runs the following tasks:

Check for state transition conditions. Footstrike and toe-off may be detected based on pressure measurements, ground reaction force measurements, acceleration, tibial orientation, or any other sensor measurement or combination of measurements.

Update sensor readings.

Calculate instantaneous knee adduction moment for knee(s) of stance leg(s).

Update derived measurements (such as knee adduction moment impulse).

Compare signal(s) of interest to context (e.g. target value, healthy population range, etc.). (See "Feedback" section.)

Calculate feedback to apply; send commands or data to feedback subsystem (See "Feedback" section.)

Log data.

Feedback

Visual Feedback

In one embodiment, a wearable device of the invention transmits data to a computer having a display (e.g., a smartphone, tablet, laptop, or desktop,) which runs an application that displays the data in a way that is informative to the user, either the wearer or a clinician. The data may either be displayed in real time, as visual feedback to the wearer as he or she walks, or in aggregate, as statistics describing past data over some time period.

Real-Time Feedback

Real-time feedback allows the wearer to observe the effect of different gait adjustments, terrain types, walking speeds, footwear, and other factors on the signals that the device measures. For instance, using real-time feedback, a user may observe that a toe-in gait results in a different peak knee adduction moment than a toe-out gait, and may experiment with a range of foot orientations to find a gait that minimizes knee adduction moment while remaining comfortable.

The user may choose from a variety of ways of viewing the data. Furthermore, the choices available to the user may be determined based on collected data that will clarify what methods most effectively change user behavior in a beneficial way. Choices available may include, for instance, which signals to present. From raw knee adduction moment as a function of time, other signals, or features, associated with instantaneous knee adduction moment, can be computed, such as peak knee adduction moment for each step, the first and second knee adduction moment peaks throughout the gait cycle, and knee adduction moment impulse, which is the integral of the knee adduction moment with respect to time over the gait cycle, as well as any other information that can be derived using the data collected by the system.

Figure 11:
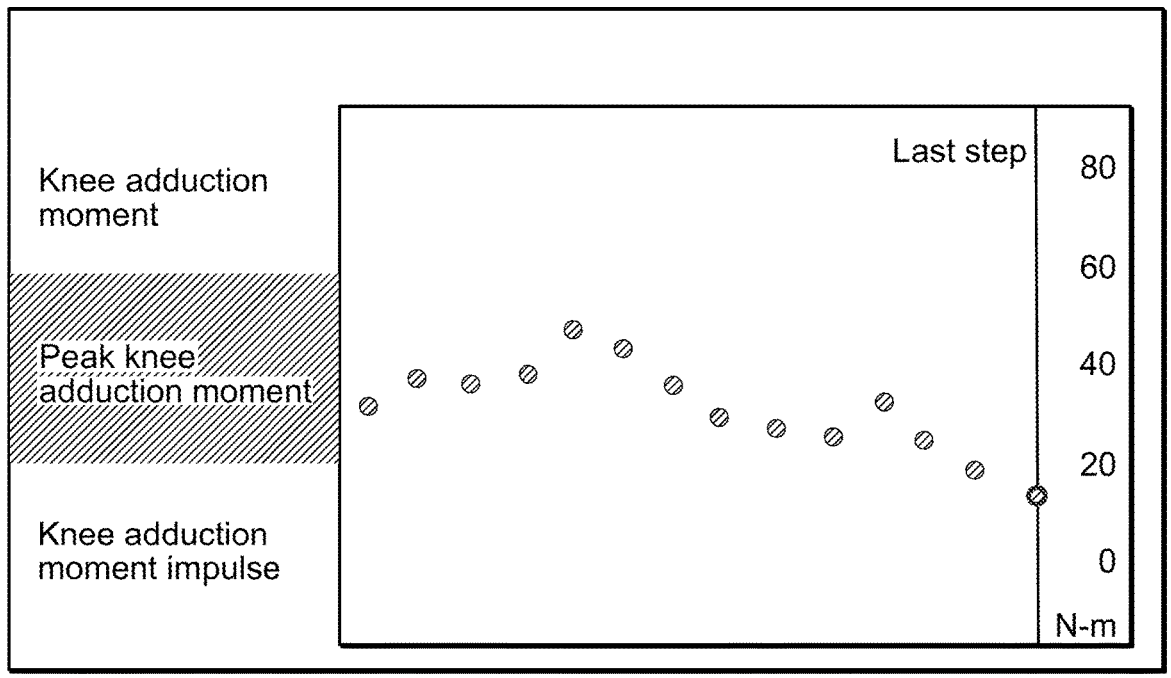
FIG. 11 is a prophetic example of real-time visual feedback according to one embodiment of the invention showing data alone.

The user may also choose a context in which to view the data, such as any of the following:

Data alone: A graph of any of the signals available, using data from the most recent steps. Some signals (e.g. peak knee adduction moment, knee adduction moment impulse) are discrete, so one value will appear per step, as shown in the prophetic example represented by FIG. 11; other signals (e.g. raw knee adduction moment) are effectively continuous (with many samples per step), so may be plotted as a continuous function of time.

Figure 12:
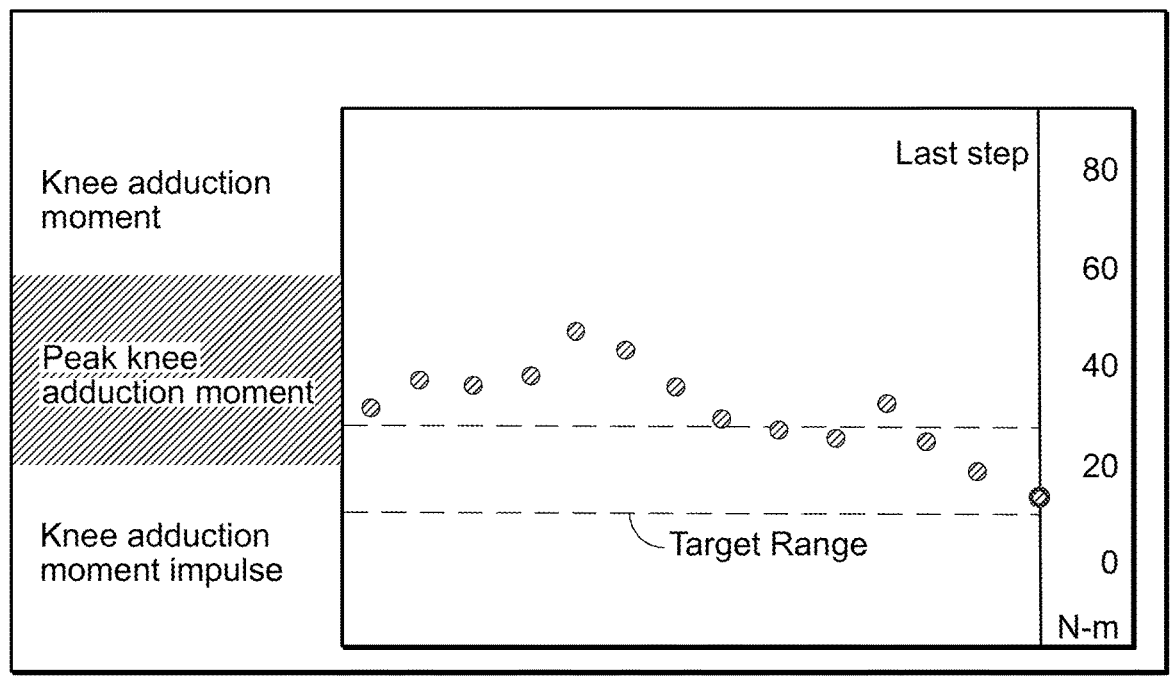
FIG. 12 is a prophetic example of real-time visual feedback according to one embodiment of the invention including a target range.
Figure 13:
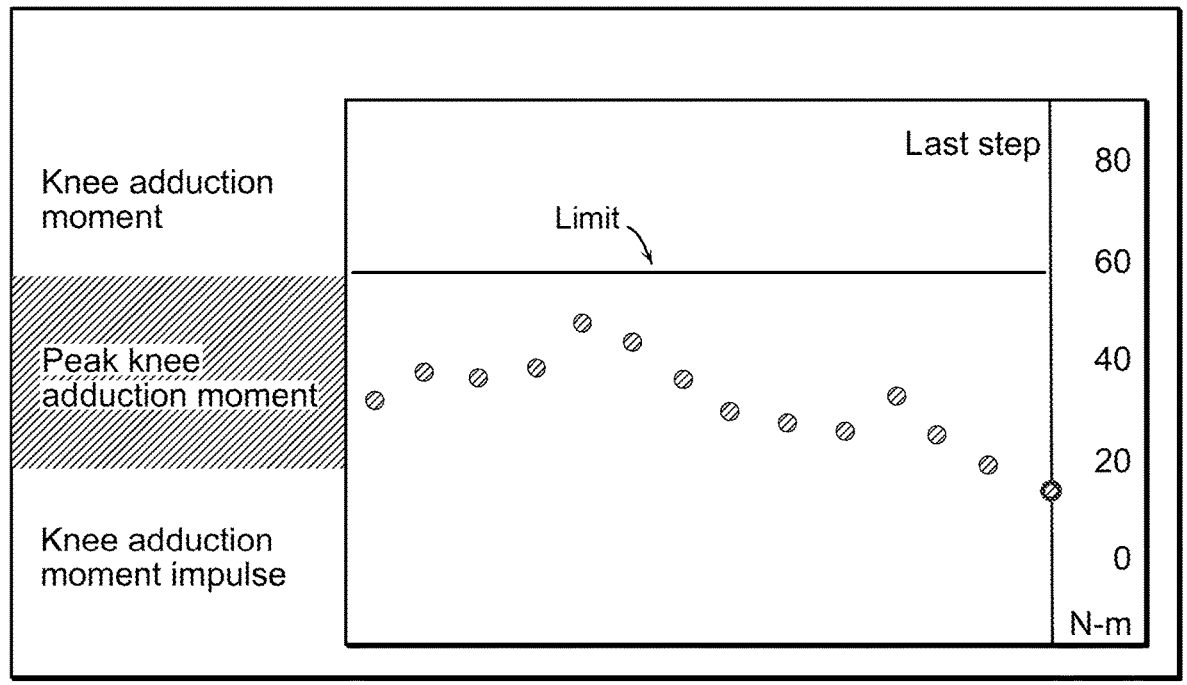
FIG. 13 is a prophetic example of real-time visual feedback according to one embodiment of the invention including a target limit.

Comparing actual measurements to a target: As shown in prophetic examples represented by FIGS. 12 and 13, the display may include a limit or range of values for the signal being displayed, in order to help the user adjust his or her gait to achieve a certain knee adduction moment. A target may also be displayed as a limit which the user will attempt to remain below.

Figure 14:
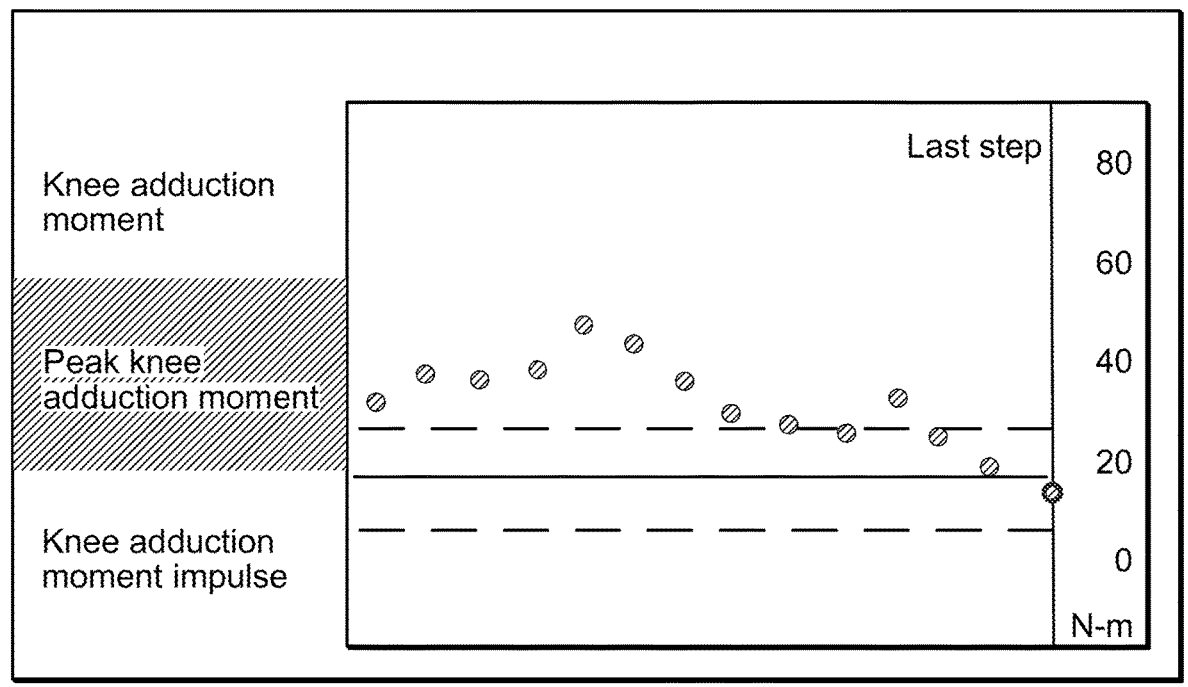
FIG. 14 is a prophetic example of real-time visual feedback according to one embodiment of the invention, with bounds indicating features of a healthy population.

In the context of a healthy matched population: Given information about the user (age, weight, height, sex), visual feedback may include information about a demographically similar, but healthy (nonosteoarthritic) population, along with the user's own data. For instance, if the wearer were a 65 year-old, 140-lb, 5'2" individual, and if the data points displayed prophetically in the display, e.g., FIG. 14, represent peak knee adduction moment on each of the wearer's most recent steps, with an average walking speed of 0.75 m/s over those steps, then the visual feedback might include, for instance, the mean and +/−1 standard deviation bounds of average peak knee adduction moment for a healthy individual of the same gender, age, weight, and height when walking at that speed, based on interpolations of appropriate data. FIG. 14 illustrates, with horizontal lines representing these healthy population statistics (solid line for the mean and dashed lines for +/−1 standard deviation bounds), one way in which this information can be presented.

Figure 15:
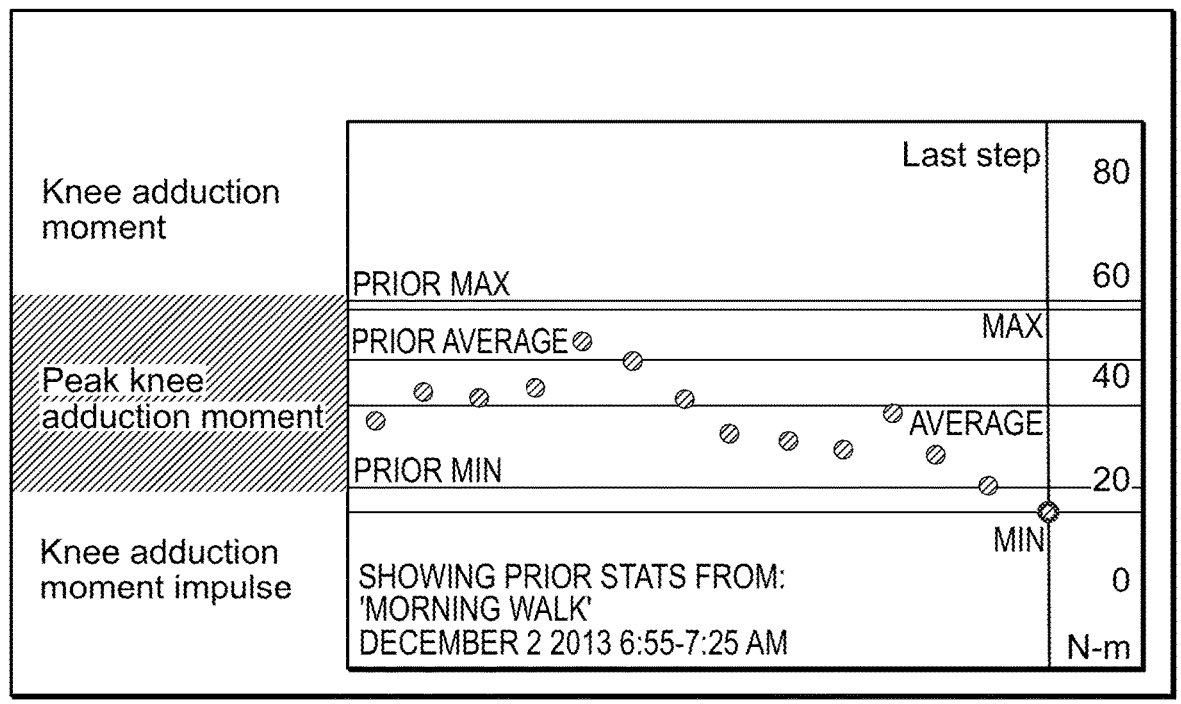
FIG. 15 is a prophetic example of real-time visual feedback according to one embodiment of the invention, with statistics from current and prior walks.

In the context of personal history: Real-time data can be shown superimposed on statistics from previous uses of the device (e.g. past walks), which the user may select. Prophetic statistics from the use in progress (e.g. an ongoing walk) are displayed in FIG. 15.

The options described above are not mutually exclusive, and could be combined in a variety of ways. While the mock-ups show "knee adduction moment," "peak knee adduction moment," and "knee adduction moment impulse" as the three signals available to view, any other signals that can be derived using the system described can naturally be displayed in a similar way.

Offline Feedback

Figure 16:
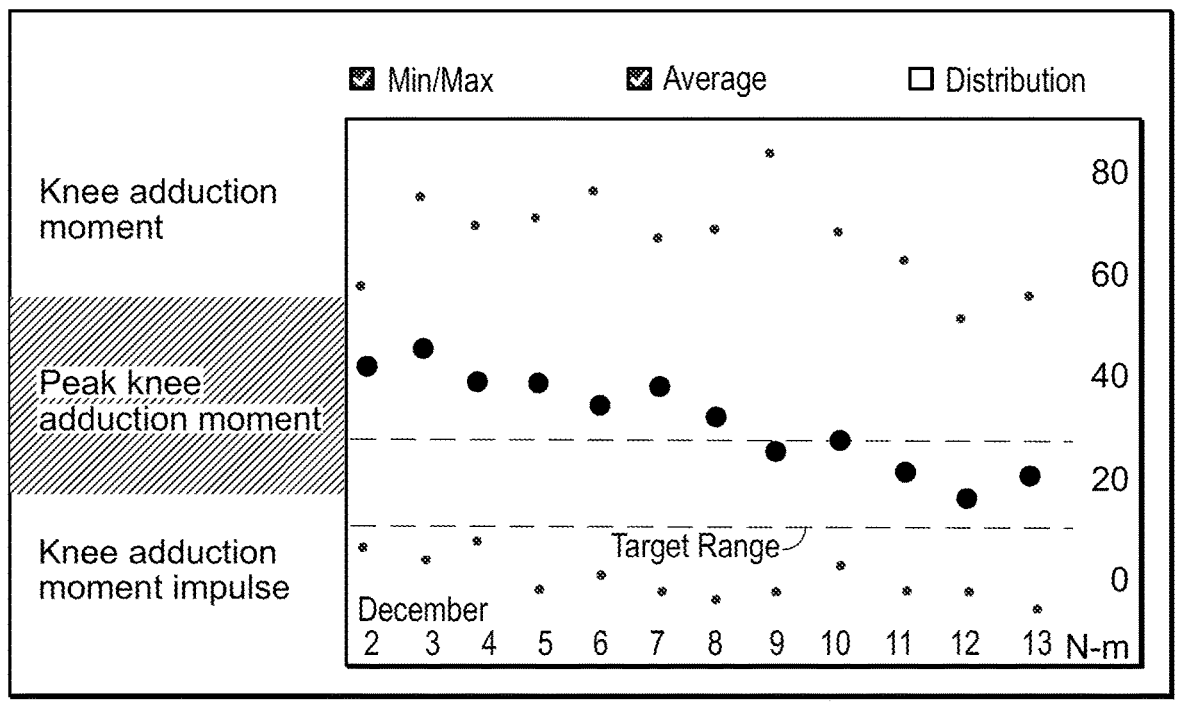
FIG. 16 is a prophetic example of offline visual feedback according to one embodiment of the invention, including a target range and daily min/max/average peak knee adduction moment values over multiple days.

In one embodiment, the wearable device of the invention stores data for the user to review offline, or for a physical therapist or immunologist to examine during an office visit. The user may select from a variety of ways to view the data. As with realtime data, measurements available include raw knee adduction moment, knee adduction moment impulse, and any other statistics derived from this information, including peak knee adduction moment per step. Data from steps may be averaged or otherwise combined to give an aggregate measurement over a certain number of steps (e.g. the maximum and minimum every ten steps) or over a certain time period (e.g. a daily minimum, a daily maximum and a daily average) illustrated prophetically, for example, in FIG. 16. Measurements may be expressed in absolute units (e.g. N-m, N-m-s), or adjusted by physical characteristics of the user; for instance, knee adduction moment may be expressed as a percentage of body mass, or as a percentage of body weight multiplied by height. All three methods appear in the literature, but Robbins, Birmingham, Maly, Chesworth, & Giffin, 2011, the relevant teachings of which are incorporated herein by reference in their entirety), suggests that nonnormalized moment is a better predictor of radiographic osteoarthritis progression than the other two.) As with real-time feedback, data may be presented alongside other information for context, such as a target value or range, average values from a healthy population and personal history.

Haptic Feedback

In still another embodiment, haptic feedback generated by the invention can convey real-time information to a walker about his or her gait, as Shull et al demonstrated in the context of a knee adduction moment reduction goal (P. B. Shull et al., 2011 the relevant teachings of which are incorporated herein by reference in their entirety). Using Vicon (motion-capture) data and a force-instrumented treadmill, the researchers measured the effect of changing various gait parameters (trunk sway, tibia angle, and foot progression) on knee adduction moment during walking. They then calculated a target set of gait parameters for each subject (minimizing "overall gait change" by their own metric), and used haptic feedback to convey an error metric to the walker in real-time. The actuators used were three vibrating motors, two on the foot and one on the knee, and one skin stretch device on the lower back.

An embodiment of the invention employs the same actuation modes, vibration and skin stretching, to convey realtime feedback to the user, using wearable sensors rather than a gait laboratory to measure knee adduction moment. While this embodiment provides feedback on an "output" signal only—e.g. knee adduction moment, knee adduction moment impulse, or some derived value—without explicitly guiding the wearer towards any specific gait modification (e.g., directing the user to increase his or her tibia angle)—it can be augmented to implement a multi-parameter gait retraining strategy similar to that used by Shull et al.

Vibration

In another embodiment, small vibrating motors, which are widely commercially available, can be employed for haptic feedback for gait modification, for example. In this embodiment, as in (P. B. Shull et al., 2011, the teachings of which are incorporated by reference in their entirety), the motor is fixed to a strap that the user attaches to his or her body, either around the knee or elsewhere, depending on what is comfortable. The motor is controlled by a microprocessor and powered by the system's power source. The motor is controlled in such a way as to convey information to the wearer about the signal of interest. There are a number of choices involved in defining a feedback strategy, such as:

Discrete- or continuous-time: Discrete-time feedback implies that on each step the motor vibrates at a single amplitude and frequency at most once per step. Continuous-time feedback implies that the motor vibrates continuously.

Event-driven or not: Event-driven feedback implies that the motor conveys information about whether a certain condition is met, such as the signal of interest exceeding a certain threshold, by turning on or off.

Amplitude and/or frequency feedback: Amplitude feedback conveys information in the amplitude of the motor vibrations. Frequency feedback conveys information in the frequency of the motor vibrations.

Digital or analog feedback: Digital feedback implies that the amplitude or frequency of the vibrations can take on only certain discrete set of values. Analog feedback implies that the amplitude or frequency of the vibrations can take on any value (within a range).

Linear or non-linear scaling: Linear scaling implies that the amplitude or frequency is proportional to the signal of interest. Non-linear scaling implies a non-linear relationship between the signal of interest and the amplitude or frequency of the vibrations.

Volume control, allowing the user to raise or lower the amplitude of vibration, is also available to the user as a dial near the main power switch for the device.

Skin-Stretch

Stanford University teams have performed several studies with proprioception and rehabilitation in mind (Bark, Wheeler, Lee, Savall, & Cutkosky, 2009; P. B. Shull et al., 2011, the relevant teachings of all of which are incorporated by reference in their entirety). In yet another embodiment of the invention, a skin-stretch device that is strapped to the body, and twists the skin in shear by means of a rotating, ultrasonic motor-driven end-effector, with two silicone pads in contact with the skin, can be employed. Both the position and the velocity of the end-effector may be used to convey information to the wearer. The lower back is a convenient place for this device, but adjustable straps make it possible to choose other locations for it.

As with a vibration motor, a skin-stretch actuator may deliver feedback in a variety of ways:

Discrete- or continuous-time: Discrete-time feedback implies that on each step the actuator stretches the skin by some amount and then returns to its neutral position. Continuous-time feedback implies that the actuator is continuously stretching the skin by an amount that varies with time.

Event-driven or not: Event-driven feedback implies that the device conveys information about whether a certain condition is met, such as the signal of interest exceeding a certain threshold, by turning on (stretching the skin by rotating away from the neutral position) or off (remaining stationary at the neutral position).

Position and/or velocity feedback: Position feedback conveys information in the position of the end effector. Velocity feedback conveys information in the end effector's velocity.

Digital or analog feedback: Digital feedback implies that the position of the end effector can take on only certain discrete set of values (though this is an idealization since the end effector cannot move instantaneously). Analog feedback implies that the end effector may move to any position (within a range).

Linear or non-linear scaling: Linear scaling implies that the amount of stretching is proportional to the signal of interest. Non-linear scaling implies a non-linear relationship between the signal of interest and the amount of stretching.

Electrical Feedback

In another embodiment of the invention, functional Electrical Stimulation (FES) can be employed as a method for gait-modification for osteoarthritis patients. FES includes placing electrodes (either surface, percutaneous, or implantable) in specific locations on the patient's leg, and activating certain muscles by applying a voltage across them. Initially developed for hemiplegic stroke patients suffering from drop-foot, systems now also exist to help paraplegics sit and stand with a balance aid, as for example, described by Peckham & Knutson, 2005, the relevant teachings of which are incorporated herein by reference in their entirety.

FES has been shown to increase propulsion (as measured by peak anterior ground reaction forces) in the paretic leg of hemiparetic patients (Kesar et al., 2009, the relevant teachings of which are incorporated herein by reference in their entirety), and could potentially be used to alter the gait of an osteoarthritis patient in such way as to reduce the knee adduction moment of the affected side(s). For instance, as mentioned earlier, it has been suggested that increased "push-off" work in a foot-ankle prosthesis is correlated with decreased first-peak knee adduction moment in the sound leg. (Morgenroth et al., 2011, the relevant teachings of which are incorporated herein by reference in their entirety).

Similarly, it is possible that stimulating the muscles in a user's leg to provide more propulsive force during walking could decrease the first-peak knee adduction moment in the opposite (osteoarthritic) leg. By measuring the knee adduction moment in real time, the system can automatically adjust the strength of the electrical stimulation to keep peak knee adduction moment below a certain level. Other gait parameters can be controlled in a similar manner by stimulating the appropriate muscle groups. FES can be applied to several muscle groups simultaneously, in order to control multiple gait parameters at once (such as propulsive force and toe inversion/eversion angle). In this case, the algorithm for determining the amplitude and timing of stimulation to each muscle group based on measured knee adduction moment levels can be fixed for all users; alternatively, the system can observe the effect of varying stimulation parameters for each individual user, and develop a minimally disruptive stimulation strategy, in the manner of (Fregly, Reinbolt, Rooney, Mitchell, & Chmielewski, 2007; P. B. Shull et al., 2011, the relevant teachings of all of which are incorporated herein by reference in their entirety).

Feedback Via Prosthesis/Orthosis/Brace

Unilateral amputees are more likely than non-amputees to suffer from knee osteoarthritis in their sound leg. (Norvell et al., 2005, the relevant teachings of which are incorporated herein by reference in their entirety). Although no reason for this relationship has been established, it has been suggested that reduced propulsion by the prosthesis during late stance could increase stress on the intact leg, and there is evidence that a prosthesis which does more work during push-off can decrease the first peak knee adduction moment in the leading leg (Morgenroth et al., 2011, the relevant teachings of which are incorporated herein by reference in their entirety). Electronic prosthetic knees and ankles, which are increasingly available to patients, help the wearer walk by modifying joint torques and impedances throughout the gait cycle. In another embodiment of the invention, peak knee adduction moment can be regulated, as well as other signals of interest, by interfacing with an electronic prosthesis so as to increase propulsive force during push-off. The same could be done with multiple prostheses, in the case of bi-lateral or trans-femoral amputees.

In yet another embodiment of the invention, an electronically-controlled lower-limb orthotic device can be employed so that propulsive force exerted by the orthosis is adjusted to regulate peak knee adduction moment in the opposite leg.

Alternatively, an orthosis (or active brace) worn on the osteoarthritic knee itself can be employed by an embodiment of the invention to apply a torque directly to the knee, in order to reduce knee adduction moment to a desired level.

While this invention has been particularly shown and described with references to example embodiments thereof, it will be understood by those skilled in the art that various changes in form and details may be made therein without departing from the scope of the invention encompassed by the appended claims.

REFERENCES

Bae, J., Kong, K., Byl, N., & Tomizuka, M. (2011). A mobile gait monitoring system for abnormal gait diagnosis and rehabilitation: a pilot study for Parkinson disease patients. *Journal of Biomechanical Engineering*. doi: 10.1115/1.4003525

Bark, K., Wheeler, J., Lee, G., Savall, J., & Cutkosky, M. (2009). A wearable skin stretch device for haptic feedback. *World Haptics 2009-Third Joint EuroHaptics Conference and Symposium on Haptic Interfaces for Virtual Environment and Teleoperator Systems*. doi:1 0.11 09/WHC.2009.481 0850

Collins, A. T., Blackburn, J. T., Olcott, C. W., Miles, J., Jordan, J., Dirschl, D. R., & Weinhold, P. S. (2011). Stochastic resonance electrical stimulation to improve proprioception in knee osteoarthritis. *The Knee*, 18, 317-322. doi:10.1016/j.knee.2010.07.001

Cook, C., Pietrobon, R., & Hegedus, E. (2007). Osteoarthritis and the impact on quality of life health indicators. *Rheumatology International*, 27(4), 315-21. doi: 1 0.1 007/s00296-006-0269-2

De Guise, J. A., Yahia, L., Duval, N., Godbout, B., Koller, A., Sati, M., . . . El Maach, I. (2007). System for the analysis of 3D kinematic of the knee. US.

De Guise, J. A., Yahia, L., Duval, N., Hagemeister, N., Parent, G., St-Onge, N., . . . El Maach, I. (2009). Method of calibration for the representation of knee kinematics and harness for use therewith.

Dowling, A. V, Fisher, D. S., & Andriacchi, T. P. (2010). Gait modification via verbal instruction and an active feedback system to reduce peak knee adduction moment. *Journal of Biomechanical Engineering*, 132(7), 071007. doi: 1 0.1115/1.4001584

Fong, D. T.-P., Chan, Y.-Y., Hong, Y., Yung, P. S.-H., Fung, K.-Y., & Chan, K.-M. (2008). Estimating the complete ground reaction forces with pressure insoles in walking. *Journal of Biomechanics*, 41, 2597-2601. doi: 10.1 016/j.jbiomech.2008.05.007

Forner Cordero, a, Koopman, H. J. F. M., & van der Helm, F. C. T. (2004). Use of pressure insoles to calculate the complete ground reaction forces. *Journal of Biomechanics*, 37(9), 1427-32. doi:10.1 016/j.jbiomech.2003.12.016

Foroughi, N., Smith, R., & Vanwanseele, B. (2009). The association of external knee adduction moment with biomechanical variables in osteoarthritis: a systematic review. *The Knee*, 16(5), 303-9. doi:1 0.1 016/j.knee.2008.12.007

Franz, J. R., Maletis, M., & Kram, R. (2014). Real-time feedback enhances forward propulsion during walking in old adults. *Clinical Biomechanics* (Bristol, Avon), 29(1), 68-74. doi:10.1016/j.clinbiomech.2013.10.018.

Fregly, B. J., Reinbolt, J. A., Rooney, K. L., Mitchell, K. H., & Chmielewski, T. L. (2007). Design of patient specific gait modifications for knee osteoarthritis rehabilitation. *IEEE Transactions on Bio-Medical Engineering*, 54(9), 1687-1695. doi:10.1109/TBME.2007.891934

Guccione, a a, Felson, D. T., & Anderson, J. J. (1990). Defining arthritis and measuring functional status in elders: methodological issues in the study of disease and physical disability. *American Journal of Public Health*, 80(8), 945-9. Retrieved from http://www.pubmedcentral.nih.gov/articlerender.fcgi?artid=1404793&tool=pmcentrez&rendertype=abstract Jackson, B. D., Wluka, A. E., Teichtahl, A. J., Morris, M. E., & Cicuttini, F. M. (2004). Reviewing knee osteoarthritis—a biomechanical perspective. Journal of Science and Medicine in Sport/Sports Medicine Australia, 7, 347-357. doi:10.1016/S1440-2440(04)80030-6

Kalman, R. E. (1960). A New Approach to Linear Filtering and Prediction Problems. Transactions of the ASME-Journal of Basic Engineering, 82, 35-45. doi:10.1115/1.3662552

Kesar, T. M., Perumal, R., Reisman, D. S. et al (2009). Functional electrical stimulation of ankle plantarflexor and dorsiflexor muscles: effects on poststroke gait. Stroke; a Journal of Cerebral Circulation, 40(12), 3821-3827.

doi:10.1161/STROKEAHA.109.560375

Minetti, A. E., Cisotti, C., & Mian, O. S. (2011). The mathematical description of the body centre of mass 3D path in human and animal locomotion. Journal of Biomechanics, 44, 1471-1477. doi:10.1016/j.jbiomech.2011.03.014

Morgenroth, D. C., Segal, A. D., Zelik, K. E. et al (2011). The effect of prosthetic foot push-off on mechanical loading associated with knee osteoarthritis in lower extremity amputees. Gait & Posture. doi:10.1016/j.gaitpost.2011.07.001

Norvell, D. C., Czerniecki, J. M., Reiber, G. E., Maynard, C., Pecoraro, J. a, & Weiss, N. S. (2005). The prevalence of knee pain and symptomatic knee osteoarthritis among veteran traumatic amputees and nonamputees. Archives of Physical Medicine and Rehabilitation, 86(3), 487-93. doi:10.1016/j.apmr.2004.04.034

Peckham, P. H., & Knutson, J. S. (2005). Functional electrical stimulation for neuromuscular applications. Annual Review of Biomedical Engineering, 7, 327-60. doi: 10.1146/annurev.bioeng.6.040803.140103

Robbins, S. M. K., Birmingham, T. B., Maly, M. R., Chesworth, B. M., & Giffin, J. R. (2011). Comparative diagnostic accuracy of knee adduction moments in knee osteoarthritis: a case for not normalizing to body size. Journal of Biomechanics, 44, 968-971. doi:10.1016/j.jbiomech.2010.12.021

Sharma, L., Hurwitz, D. E., Thonar, E. J. et al (1998). Knee adduction moment, serum hyaluronan level, and disease severity in medial tibiofemoral osteoarthritis. Arthritis and Rheumatism, 41, 1233-1240. doi:10.1002/1529-0131 (199807)41:7<1233::AID-ART14>3 0.0. CO<http:// 3.0.CO>; 2-L Shull, P. B., Lurie, K. L., Cutkosky, M. R., & Besier, T. F. (2011). Training multi-parameter gaits to reduce the knee adduction moment with data-driven models and haptic feedback. Journal of Biomechanics, 44(8), 1605-9. doi: 10.1016/j.jbiomech.2011.03.016

Weinstein, A. M., Rome, B. N., Reichmann, W. M. et al (2013). Estimating the burden of total knee replacement in the United States. The Journal of Bone and Joint Surgery. American Volume, 95(5), 385-92. Retrieved from http://www.ncbi.nlm.nih.gov/pubmed/23344005

Wheeler, J. W., Shull, P. B., & Besier, T. F. (2011). Real-time knee adduction moment feedback for gait retraining through visual and tactile displays. Journal of Biomechanical Engineering, 133(4), 041007. doi: 10.1115/1.4003621

Zhao, D., Banks, S. A., Mitchell, K. H., Lima, D. D. D., Jr, C. W. C., & Fregly, B. J. (2007). Correlation between the Knee Adduction Torque and Medial Contact Force for a Variety of Gait Patterns, (June), 789-797. doi:10.1002/jor Zheng, R., Liu, T., Inoue, Y., Shibata, K., & Liu, K. (2008). Kinetics Analysis of Ankle, Knee and Hip Joints Using a Wearable Sensor System. Journal of Biomechanical Science and Engineering, 3(3), 343-355. doi: 1 0.1299/jbse.3.343

The relevant teachings of all references cited herein are incorporated by reference in their entirety.

What is claimed is:

1. A method for modulating knee adduction moment of an untethered human during gait, comprising:
   with an autonomous wearable device comprising a controller and an interface linked to the controller, the interface including an actuator configured to be in communication with the human,
   a) during the gait, determining a knee adduction moment during a stance phase of a gait cycle of the untethered human, the determining the knee adduction moment including estimating a three-dimensional ground reaction force and a center of pressure based on pressure measurement from a pressure-sensing insole and determining a position of a knee joint relative to the center of pressure from relative positions of a tibia and a foot of the human;
   b) determining at least one feature associated with the knee adduction moment of the untethered human during the gait cycle; and
   c) transmitting feedback derived from the at least one feature through the interface to the human, the transmitting including adapting mechanical dynamics of the actuator to thereby modulate knee adduction moment of the untethered human during the gait.

2. The method of claim 1, further including deriving feedback from the at least one feature.

3. The method of claim 2, wherein the feedback is derived by comparing the at least one feature to a value.

4. The method of claim 3, wherein the value is a target value.

5. The method of claim 2, wherein the at least one feature is at least one member selected from the group consisting of a peak, a rise-time to a peak, a time period between first and second peaks, and impulse of the knee adduction moment.

6. The method of claim 5, further including identifying a transition condition indicating commencement of a phase of the gait cycle.

7. The method of claim 1, wherein the knee adduction moment is determined from at least one parameter of the group consisting of center of pressure, ground reaction force, acceleration, tibial orientation, femur orientation and a combination or a derivative thereof.

8. The method of claim 7, wherein the at least one parameter is measured by at least one sensor selected from the group consisting of an accelerometer, a gyroscope, a magnetometer, an optical sensor, an ultrasound transducer or sensor, a pressure sensor and a goniometer.

9. The method of claim 7, further including employing a sensor fusion algorithm to combine information from a plurality of sensors or sensor types.

10. The method of claim 9, wherein the sensor fusion algorithm includes a Kalman filter.

11. The method of claim 1, wherein estimating the three-dimensional ground reaction force includes estimating a horizontal component of the three-dimensional ground reaction force from a vertical ground reaction force and a position of a center of mass with respect to the center of pressure of the untethered human gait cycle.

12. The method of claim 11, wherein the position of the center of mass with respect to the center of pressure of the human includes a height of the center of mass and a horizontal distance between the center of mass and the center of pressure.

13. The method of claim 12, wherein the knee adduction moment is calculated by employing at least one member of the group consisting of tibia length, femur length, hip width, foot length, body height and body weight.

14. The method of claim 13, wherein the horizontal component of the three-dimensional ground reaction force is estimated at an angular momentum about the center of mass of the untethered human of about zero during the gait cycle of the untethered human.

15. The method of claim 14, wherein the pressure-sensing insole comprises a plurality of sensors and the vertical ground reaction force is measured as a weighted sum of pressure measurements from the insole sensors.

16. The method of claim 15, wherein the center of mass is estimated as a function of a fixed anatomical position.

17. The method of claim 15, wherein the center of mass is estimated as a function of a fixed periodic trajectory with respect to an anatomical reference point.

18. The method of claim 14, further including determining the relative position of a knee joint center and the center of mass with respect to the center of pressure of the human.

19. The method of claim 1, wherein determining the knee adduction moment further includes measuring a joint angle of the knee joint.

20. The method of claim 19, wherein the joint angle is measured in at least one of one, two and three dimensions.

21. The method of claim 20, wherein the joint angle is measured by employing a goniometer attached to the knee joint.

22. The method of claim 21, wherein determining the knee adduction moment further includes measuring angular velocity of the knee joint.

23. The method of claim 1, wherein the relative positions are measured by magnetometers mounted on the human.

24. The method of claim 1, further including attaching tibia and femur inertial measurement units (IMUs) to each leg of the individual, and employing the IMUs to define a tibial IMU frame, a femoral IMU frame and a world frame to thereby obtain the knee adduction moment.

25. The method of claim 20, further including updating determination of the at least one feature.

26. The method of claim 25, wherein determining the at least one feature of knee adduction includes calculating knee adduction moment impulse by integrating the determined knee adduction moment with respect to time over the gait cycle of the untethered human.

27. The method of claim 1, wherein the interface includes at least one member selected from the group consisting of a vibrating motor, a skin-stretch device, a functional electrical stimulation (FES) device, an orthotic device, and a lower limb prosthesis that adapts its shape, behavior or mechanical dynamics to alter knee adduction moment.

28. An autonomous wearable device for modulating knee adduction moment of an untethered human during gait, the autonomous wearable device including a controller and an interface linked to the controller, comprising:
  a) wearable means for determining a knee adduction moment during a stance phase of a gait cycle of the untethered human during the gait, the determining the knee adduction moment including estimating a three-dimensional ground reaction force and a center of pressure based on one or more pressure measurements from a pressure-sensing insole and determining a position of a knee joint relative to the center of pressure from relative positions of a tibia and a foot of the human;
  b) wearable means for determining at least one feature associated with the knee adduction moment of the untethered human during the gait cycle; and
  c) wearable means for transmitting feedback derived from the at least one feature through the interface to the human, the interface including an actuator configured to be in communication with the human, the transmitting including adapting mechanical dynamics of the actuator to thereby modulate knee adduction moment of the untethered human during the gait.

29. The autonomous wearable device of claim 28, further including wearable means for deriving feedback from the at least one feature.

* * * * *